(12) United States Patent
Tian et al.

(10) Patent No.: US 11,382,738 B2
(45) Date of Patent: Jul. 12, 2022

(54) SYSTEM AND METHOD FOR IMPLANTING AND SECURING A BIOPROSTHETIC DEVICE TO WET TISSUE

(71) Applicant: Edwards Lifesciences Corporation, Irvine, CA (US)

(72) Inventors: Bin Tian, Irvine, CA (US); Rodolfo Rodriguez, Costa Mesa, CA (US); Louis A. Campbell, Santa Ana, CA (US); Steven M. Claessens, Long Beach, CA (US); Carolyn Sue Martinez, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 158 days.

(21) Appl. No.: 16/570,797

(22) Filed: Sep. 13, 2019

(65) Prior Publication Data
US 2020/0000586 A1    Jan. 2, 2020

Related U.S. Application Data

(60) Provisional application No. 62/506,253, filed on May 15, 2017, provisional application No. 62/474,973, filed on Mar. 22, 2017.

(51) Int. Cl.
*A61F 2/24* (2006.01)

(52) U.S. Cl.
CPC .......... *A61F 2/2418* (2013.01); *A61F 2/2433* (2013.01); *A61F 2/2445* (2013.01);
(Continued)

(58) Field of Classification Search
CPC .... A61F 2/2409; A61F 2/2418; A61F 2/2427; A61F 2/2442; A61F 2/2445;
(Continued)

(56) References Cited

U.S. PATENT DOCUMENTS 4,868,237 A * 9/1989 Hoff ................... A61B 17/8802
                                                         524/407
5,707,647 A * 1/1998 Dunn ................... A61K 9/0024
                                                         128/898
(Continued)

FOREIGN PATENT DOCUMENTS

| EP | 2298243 A1 | 3/2011 | |
| WO | 2015175662 A1 | 11/2015 | |
| WO | WO-2018175619 A1 * | 9/2018 | ........... A61F 2/2445 |

*Primary Examiner* — Paul B Prebilic
(74) *Attorney, Agent, or Firm* — Darren M. Franklin; Michelle Kim; Sheppard, Mullin, Richter & Hampton LLP

(57) ABSTRACT

Systems, devices, kits, and methods are described for securing a bioprosthetic heart valve within an anatomical feature of a patient. Kits can comprise a bioprosthetic heart valve, a curable composition, and an applicator configured to deliver the curable composition to a target area. The bioprosthetic heart valve can comprise a support structure and one or more valve leaflets coupled thereto. The support structure can comprise a sewing portion peripheral of the bioprosthetic heart valve. The support structure and the valve leaflets can define a central flow orifice. The curable composition can comprise a pre-polymer composition and an initiator. Methods can comprise positioning the bioprosthetic heart valve within the anatomical feature of a patient, applying the curable composition to one or both of the bioprosthetic heart valve and the anatomical feature, and curing the curable composition for a cure time. The applying can be performed before or after the positioning.

33 Claims, 31 Drawing Sheets

(52) U.S. Cl.
CPC ............. *A61F 2210/0085* (2013.01); *A61F 2220/0008* (2013.01); *A61F 2220/0075* (2013.01); *A61F 2240/001* (2013.01); *A61F 2250/0001* (2013.01); *A61F 2250/0069* (2013.01)

(58) Field of Classification Search
CPC ...... A61F 2210/0085; A61F 2220/0008; A61F 2220/005; A61F 2220/0075; A61F 2240/001; A61F 2250/0001; A61F 2250/0069
See application file for complete search history.

(56) References Cited

U.S. PATENT DOCUMENTS

| | | | | |
|---|---|---|---|---|
| 5,957,949 | A * | 9/1999 | Leonhardt | A61F 2/2436 |
| | | | | 623/1.24 |
| 6,780,510 | B2 * | 8/2004 | Ogle | A61L 24/046 |
| | | | | 428/413 |
| 2006/0020333 | A1 | 1/2006 | Lashinski et al. | |
| 2006/0148923 | A1 | 7/2006 | Ashman et al. | |
| 2008/0004686 | A1 | 1/2008 | Hunt et al. | |
| 2011/0098802 | A1 * | 4/2011 | Braido | A61F 2/2409 |
| | | | | 623/1.26 |
| 2012/0078357 | A1 * | 3/2012 | Conklin | A61F 2/2412 |
| | | | | 623/2.18 |
| 2014/0046435 | A1 | 2/2014 | Yeung et al. | |
| 2015/0335321 | A1 * | 11/2015 | Edelman | A61F 2/95 |
| | | | | 623/1.11 |
| 2016/0310268 | A1 | 10/2016 | Oba et al. | |

* cited by examiner

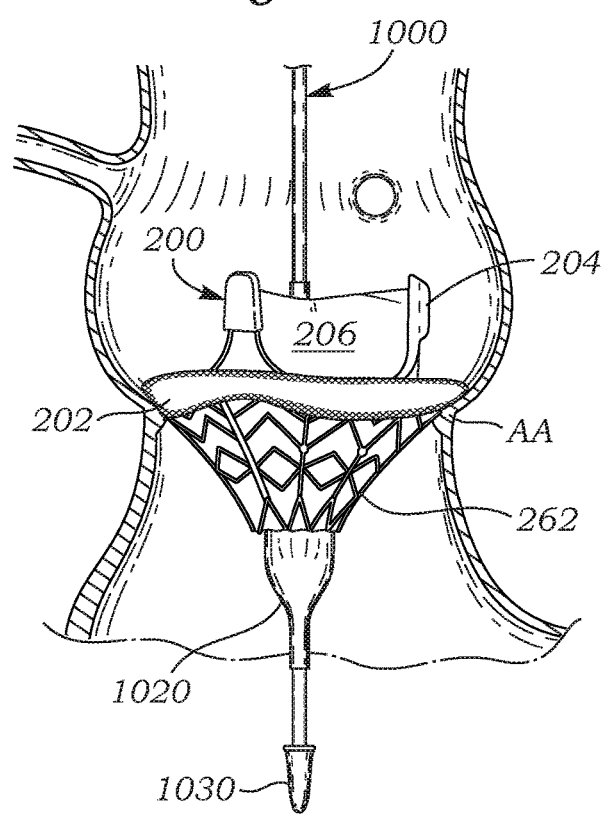
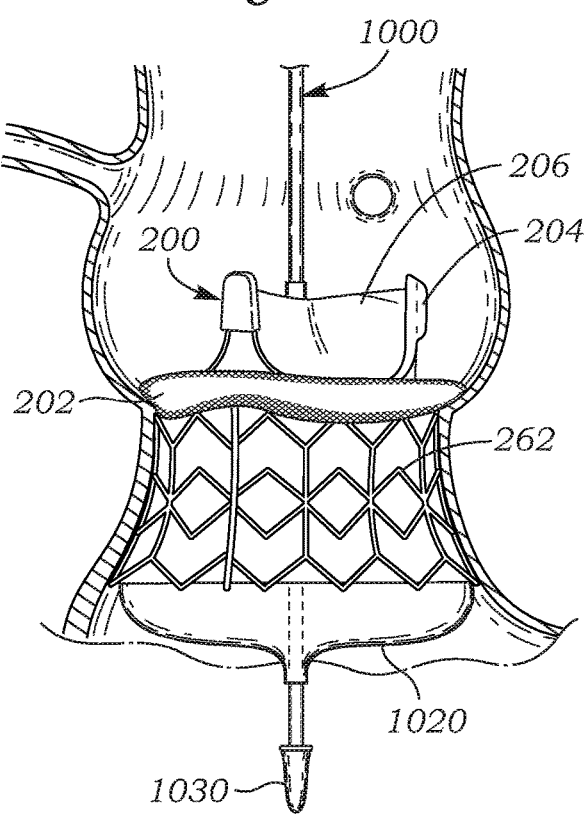

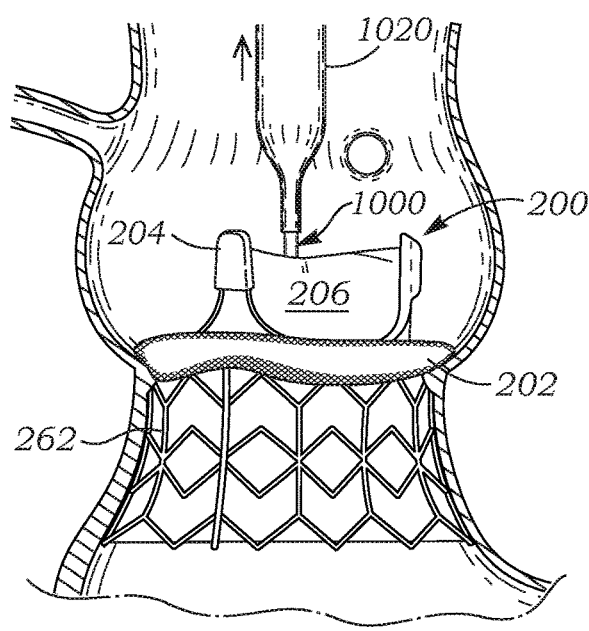 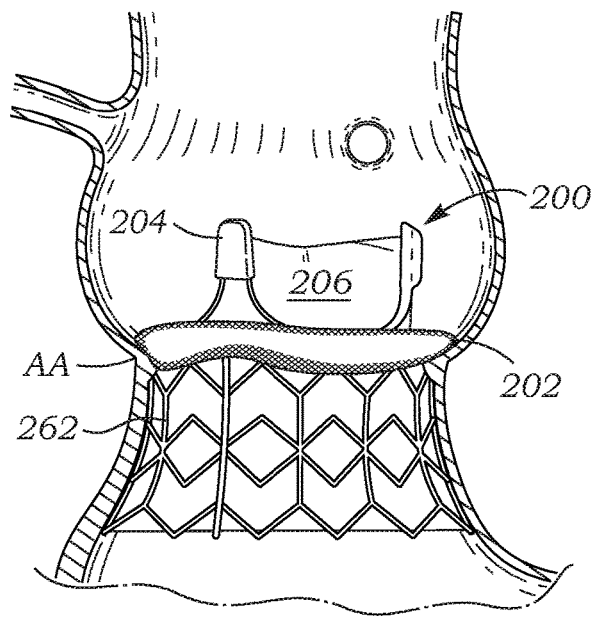

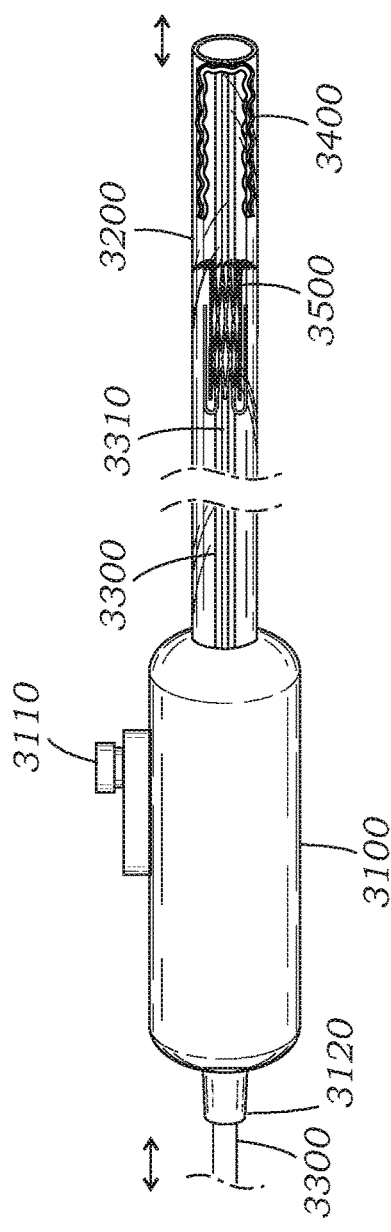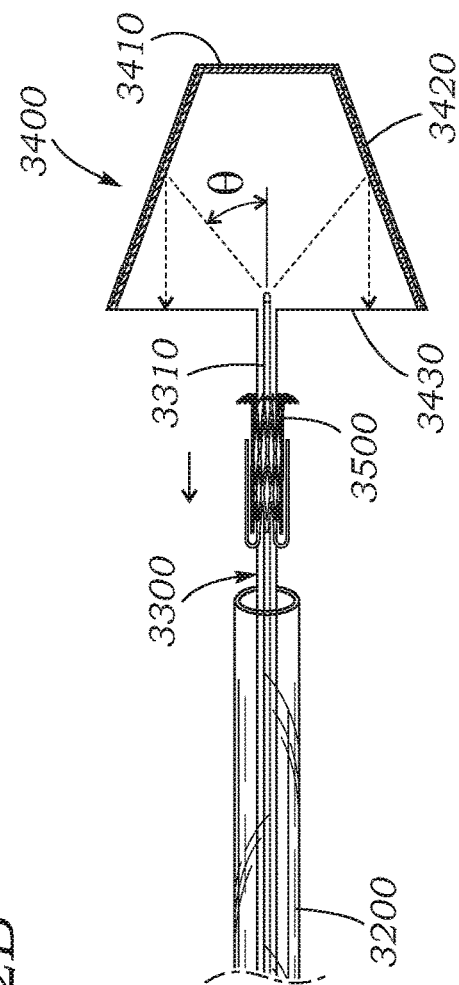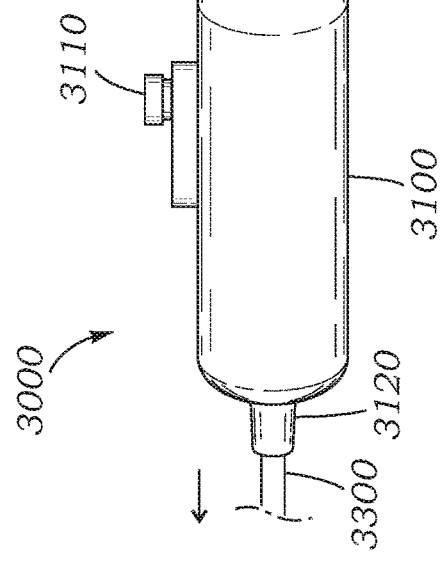
Fig. 12A
Fig. 12B

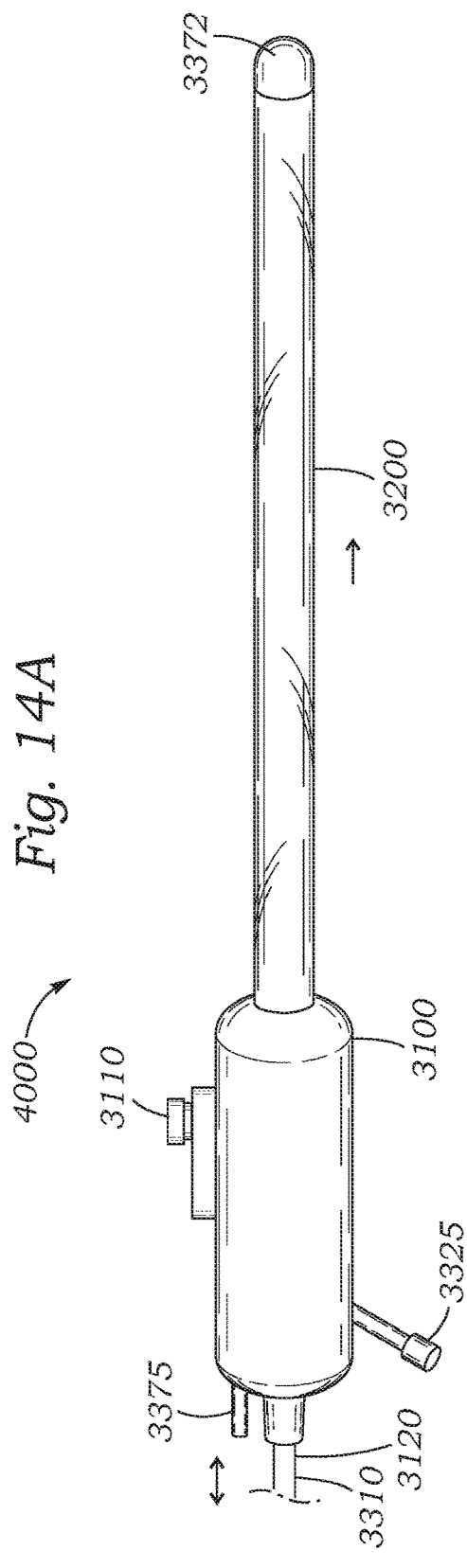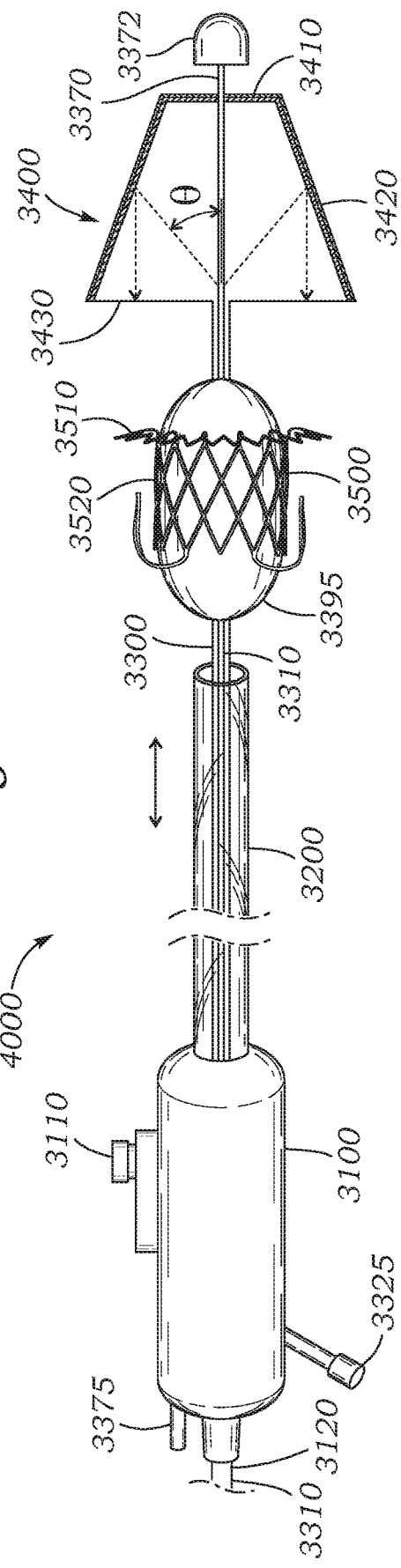

SYSTEM AND METHOD FOR IMPLANTING AND SECURING A BIOPROSTHETIC DEVICE TO WET TISSUE

CROSS-REFERENCE TO RELATED APPLICATIONS

This application is a continuation of PCT Patent Application No. PCT/US2018/023610, filed Mar. 21, 2018, which claims priority to U.S. Provisional Patent Application No. 62/474,973, filed Mar. 22, 2017, and to U.S. Provisional Patent Application No. 62/506,253, filed May 15, 2017, the entire contents of which are incorporated by reference into this application.

FIELD OF THE INVENTION

This invention relates to systems and methods for implanting a bioprosthetic device in a patient, including, for example, to systems and methods for securing and/or sealing a bioprosthetic heart valve to an anatomical feature of a patient.

BACKGROUND

There are numerous challenges associated with the implantation of bioprosthetic devices within a human body. Among these challenges is the ability to successfully secure the bioprosthetic device to the tissue such that the device does not migrate or move from its target position after implantation.

The challenges are significant for replacement bioprosthetic heart valves, which are implanted in a hemodynamic environment and are continuously subjected to the forces resulting from the pulsatile blood flow generated by the heart. Additionally, replacement bioprosthetic heart valves do not readily adhere to wet tissue substrates and therefore require the additional steps of securing the bioprosthetic heart valves within the tissue annulus. This securing can be accomplished by suturing the bioprosthetic heart valve to the tissue annulus. This can also be accomplished by designing the bioprosthetic heart valve to expand and exert a sufficient amount of radial force to secure it within the tissue annulus. Bioprosthetic heart valve designs can include an expandable frame or stent to which a valve structure can be secured.

While sutures and/or radial force can be effective in securing the bioprosthetic heart valves to the tissue annulus, they can also be ineffective in addressing other complications associated with implanted bioprosthetic heart valves. Perivalvular leakage (PVL) is one complication that occurs when blood flows through a channel or gap between the structure of an implanted heart valve and the cardiac or arterial tissue due to a lack of appropriate sealing. PVL has been shown to greatly affect the clinical outcome of aortic valve replacement procedures, and the severity of perivalvular leakage has been correlated with patient mortality.

What is therefore needed is a replacement bioprosthetic heart valve that adheres to the surrounding cardiac or arterial tissue so as to secure it from movement after implantation and that also provides appropriate sealing to prevent or reduce the likelihood of PVL in the patient.

BRIEF SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways.

Methods for implanting an implant device (e.g., a prosthetic device, a bioprosthetic device, a heart valve, a bioprosthetic heart valve, a stent, a graft, an annuloplasty ring, etc.) to an anatomical feature (e.g., tissue, a native annulus, vasculature, etc.) of a patient are provided. The method(s) can comprise any one or more of the following steps. The implant device can be positioned at an implant location inside the patient's body. The implant device can comprise a sewing portion disposed peripherally of the implant device. A curable composition can be applied to one or both of the implant device and an anatomical feature. The curable composition can comprise a pre-polymer composition and an initiator. The curable composition can be cured for a cure time after the applying step. The applying step can be performed either before or after the positioning.

The implant device can be selected from the group consisting of: a heart valve, bioprosthetic heart valve, stent, graft, an annuloplasty ring, other implants, or subsets of this group. The implant device can be a heart valve that can comprise a support structure and one or more valve leaflets coupled to the support structure. The support structure can define a central flow orifice. The implant device can further comprise a stent frame having a first end coupled to the support structure and a second end extending away from the support structure. At least a portion of the stent frame can be covered by a stent frame fabric.

The curable composition can be applied to one or more selected from the group consisting of: the support structure, sewing portion, stent frame, stent frame cover/fabric, and the anatomical feature.

Optionally, the applying step can be performed before the positioning and/or after the positioning. Also, the applying can be performed by one or a combination of the following: (1) dipping one or more of the support structure, sewing portion, stent frame, and stent frame cover/fabric into the curable composition; (2) applying the curable composition via an injector/applicator onto one or more of the support structure, sewing portion, stent frame, and stent frame cover/fabric; (3) applying a layer of the curable composition around one or more of the support structure, sewing portion, stent frame, and stent frame cover/fabric; and (4) applying a layer of the curable composition directly onto the anatomical feature.

When applied after the positioning, the applying can be performed by one a combination of: (1) applying the curable to an interface between the implant device and the anatomical feature; and (2) injecting the curable into an implant area between the implant device and the anatomical feature.

An injector/applicator can be delivered to an implant area between the implant device and the anatomical feature after the positioning and before the applying, and the applying can comprise extruding the curable composition from the injector to the implant area. The injector/applicator can comprise an extrusion tip. The extrusion tip can be and/or include a portion that is angled or hooked.

The implant device can be a heart valve or bioprosthetic heart valve comprising a central flow orifice. In one embodiment, the extrusion tip can be passed through the central flow orifice of the implant device or heart valve and can be positioned either at the interface between the implant device/heart valve and the anatomical feature or between the implant device/heart valve and the anatomical feature.

The curing can be performed in the presence of one or more of an electromagnetic energy, thermal energy, or other energy. The electromagnetic energy can be UV light or blue light. The cure time can be selected from the group consisting of: less than 30 seconds, less than 20 seconds, less than 10 seconds, less than 5 seconds, less than 2 seconds, and/or other times disclosed elsewhere in this disclosure.

The implant device can be a heart valve or bioprosthetic heart valve that can comprise a substrate onto which the curable composition/compound can be applied. The substrate can be at least one of a transparent material, porous material, woven material, and/or an open-weave material that permits a transmittance of electromagnetic energy therethrough. For example, the substrate can be an open-weave fabric having a transmittance of: at least 5%, at least 10%, at least 20%, at least 30%, at least 40%, at least 50%, at least 60%, at least 70%, at least 80%, at least 90%, or 100%, and/or other values disclosed elsewhere in this disclosure.

Each feature or concept outlined above is independent, and can be combined with the other features or concepts outlined above or with any other feature or concept disclosed in this application.

The methods described herein can include providing, obtaining, using, etc. a kit.

According to various embodiments, a kit can comprise any one or a combination of an implant device, a curable composition, an applicator, one or more extrusion tip(s), and/or other components/features. The implant device can be the same as or similar to various implant devices described above and/or shown or described elsewhere in this disclosure. Optionally, the implant device can comprise a peripherally disposed sewing portion. The kit can further comprise an energy source (e.g., an electromagnetic energy source, a thermal energy source, a light source, an ultra violet ("UV") light source, etc.). The energy source (e.g., UV light source, etc.) can be disposed on one of the following: (1) a probe; (2) inside a balloon catheter; and/or (3) around a circular support element.

The implant device can be selected from the group consisting of: a heart valve, bioprosthetic heart valve, stent, graft, an annuloplasty ring, other implants, or subsets of this group. The implant device can be a heart valve, and the heart valve can comprise a support structure and one or more valve leaflets coupled to the support structure. The support structure can define a central flow orifice.

Optionally, the implant device/heart valve can further comprise one or both of: (1) a sewing portion disposed peripherally of the implant/heart valve; and (2) a stent frame having a first end coupled to the support structure and a second end extending away from the support structure, at least a portion of the stent frame being covered by a stent frame cover/fabric. The cover/fabric can be transparent, porous, woven, and/or have an open-weave pattern.

The curable compound used in any of the methods, systems, apparatuses, devices, etc. herein can comprise or consist of a sealant that can be used to form a seal between the implant device/heart valve and the anatomical feature following the curing.

The curable compound used in any of the methods, systems, apparatuses, devices, etc. herein can comprise or consist of an adhesive that can be used to secure the implant device/heart valve to the anatomical feature without sutures after the curing.

The curable composition can be the same as or similar to curable compositions described above and/or elsewhere in this disclosure. For example, the curable composition can comprise a pre-polymer composition and an initiator. The applicator and/or extrusion tip(s) can be the same as or similar to other applicators and extrusion tips described above and/or shown or described elsewhere in this disclosure. For example, the applicator can be configured to deliver the curable composition to a desired location.

The pre-polymer composition of a curable composition can be activated by one or more functional groups that can be reacted to form crosslinks between polymer chains. The pre-polymer is optionally not activated/activatable by biological fluids. The pre-polymer can be hydrophobic. Optionally, the pre-polymer can be activated with acrylate groups. The pre-polymer can have one or more of the following characteristics before curing: (1) a degree of activation of less than about 0.2; (2) a molecular weight of less than about 1,000 Daltons; (3) a viscosity of more than 100 Pa·s; and (4) any other characteristics described with respect to pre-polymers elsewhere in this disclosure. In one embodiment, the pre-polymer can have one or more of the following characteristics before curing: (1) a degree of activation of greater than 0.2; (2) a molecular weight of greater than about 1,000 Daltons; and (3) a viscosity of less than 100 Pa·s. The pre-polymer can be the same as pre-polymers disclosed elsewhere in this disclosure.

The pre-polymer can be formed by the reaction of a polyol and a polyacid. The polyol can comprise one or more selected from the group consisting of: diols, alkane diols, triols, glycerol, trimethylolpropane, triethanolamine, tetraols, erythritol, pentaerythritol, sorbitol, unsaturated diols, tetradeca-2,12-diene-1,1,14-diol, macromonomer diols, polyethylene oxide, and N-methyldiethanolamine. The polyacid can comprise one or more selected from the group consisting of: diacid, glutaric acid, adipic acid, pimelic acid, sebacic acid, suberic acid, and azelaic acid. Optionally, the pre-polymer can be formed by the polycondensation of glycerol and sebacic acid.

The initiator of a curable composition can be a photoinitiator. The initiator can be one or more selected from the group consisting of: 2-dimethoxy-2-phenyl-acetophenone, 2-hydroxy-1-[4-(hydroxyethoxy)phenyl]-2-methyl-1-propanone (IRGACURE® 2959), 1-hydroxycyclohexyl-1-phenyl ketone (IRGACURE® 184), 2-hydroxy-2-methyl-1-phenyl-1-propanone (DAROCUR® 1173), 2-benzyl-2-(dimethylamino)-1-[4-morpholinyl)phenyl]-1-butanone (Irgacure 369), methylbenzoylformate (DAROCUR® MBF), oxy-phenyl-acetic acid-2-[2-oxo-2-phenyl-acetoxyethoxy]-ethyl ester (IRGACURE® 754), 2-methyl-1-[4-(methylthio)phenyl]-2-(4-morpholinyl)-1-propanone (IRGACURE® 907), diphenyl(2,4,6-trimethylbenzoyl)-phosphine oxide (DAROCUR® TPO), phosphine oxide, and phenyl bis(2,4,6-trimethyl benzoyl) (IRGACURE® 819). The initiator can be the same as initiators disclosed elsewhere in this disclosure.

Optionally, the pre-polymer composition and the initiator can be provided in separate chambers.

Where the curable composition comprises a sealant, the sealant can have one or more of the following characteristics after curing: (1) a crosslinking density of less than about 1%; (2) an adhesive strength of less than about 0.5 N/cm$^2$; and (3) any other characteristics described with respect to pre-polymers elsewhere in this disclosure. In one embodiment, the sealant can have one or more of the following characteristics after curing: (1) a crosslinking density of greater than about 1%; and (2) an adhesive strength of greater than about 0.5 N/cm$^2$.

The applicator(s) used in any of the methods, systems, apparatuses, devices, etc. herein can be an injector and the injector can comprise an extrusion tip or multiple extrusion tips. The extrusion tip(s) can have one or more of: (1) an angled end; (2) a hooked end; and (3) a plurality of alternating vanes disposed within an interior of the extrusion tip. The applicator can be configured to house a cartridge comprising the pre-polymer and the initiator. The applicator can comprise a pressure regulator to control a rate at which the curable composition is extruded out of the cartridge.

Each feature or concept outlined above is independent, and can be combined with the other features or concepts outlined above or with any other feature or concept disclosed in this application.

The methods described herein can include providing, obtaining, using, etc. a delivery system. For example, a delivery system for delivering and implanting an implant device (e.g., a heart valve or other implant device described herein) at a desired anatomical feature can be provided, obtained, and/or used.

According to various embodiments, a delivery system can comprise one or a combination of one or more of a delivery handle, a delivery catheter having a proximal end and a distal end, a first inflatable balloon, an implant device (e.g., a heart valve, etc.) disposed around the delivery catheter, an energy source, and other components/features. The delivery catheter can include an inner lumen between the proximal and distal ends. The first inflatable balloon can be disposed at the distal end of the delivery catheter. The implant device (e.g., heart valve) can comprise a shape-memory material and can be compressed around the delivery catheter prior to implantation.

The energy source(s) used in any of the methods, systems, apparatuses, devices, etc. herein can be movably disposed within the inner lumen of the delivery catheter. Optionally, the energy source can be a fiber optic and the fiber optic can deliver UV light out of a distal tip of the fiber optic. The energy source, fiber optic, and/or distal tip can be configured such that UV light can be emitted out of the fiber optic (e.g., the distal tip of the fiber optic) at an angle θ of about 20° to about 50° relative to a central axis.

The inflatable balloon(s) used in any of the methods, systems, apparatuses, devices, etc. herein can include a cavity that is in fluid communication with the inner lumen of the delivery catheter. The implant device (e.g., heart valve) can be disposed around the delivery catheter between the inflatable balloon and the proximal end of the delivery catheter. Optionally, the inflatable balloon can further comprise a UV-light reflective surface and a UV-light transmissive surface. The inflatable balloon can have a frusto-conical shape having a narrow distal end, a wide proximal end and an angled side wall between the narrow distal end and the wide proximal end. The UV-light reflective surface can be provided across at least a portion of the narrow distal end and the angled side wall of the inflatable balloon. The UV-light transmissive surface can be provided across at least a portion of the wide proximal end of the inflatable balloon. Optionally, all or a portion of the delivery catheter or surface thereof can also be UV-light transmissive.

The delivery handle can further comprise an actuator for advancing and retracting the energy source within the inner lumen of the delivery catheter. The actuator can advance and retract the energy source in a discrete, step-wise manner.

Optionally, the delivery system(s) herein can further comprise a second inflatable balloon disposed between the delivery catheter and the implantable heart valve. The implantable heart valve can be compressed around the second inflatable balloon when the second inflatable balloon is in a deflated state. The implantable heart valve can be in an expanded state when the second inflatable balloon is in an inflated state.

Optionally, the inner lumen of the delivery catheter can comprise a plurality of lumens. The plurality of lumens can be concentric and/or arranged in a variety of patterns. Optionally, the plurality of lumens can be arranged side-by-side or in other adjacent configurations.

Each feature or concept outlined above is independent, and can be combined with the other features or concepts outlined above or with any other feature or concept disclosed in this application.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention can be made without departing from the spirit thereof, and the invention includes all such modifications.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers can be reused to indicate correspondence between reference elements.

FIGS. 1A-1I are perspective views of exemplary embodiments of some of the different types of implant devices, which can be used in connection with the curable composition described herein, in which:

FIG. 1A is a perspective view of an exemplary embodiment of a replacement surgical aortic valve;

FIG. 1B is a perspective view of another exemplary embodiment of a replacement surgical aortic valve with a portion of the fabric cut away to show the frame stent;

FIG. 1C is a perspective view of an exemplary embodiment of a transcatheter valve;

FIGS. 1D and 1E are perspective views of another exemplary embodiment of a transcatheter valve in a compressed state for delivery and an expanded state for implantation, respectively;

FIG. 1F is a perspective view of a further exemplary embodiment of a transcatheter valve;

FIG. 1G is a perspective view of an exemplary embodiment of a replacement mitral valve; and FIGS. 1H and 1I are perspective and partial cross-sectional views, respectively, of an exemplary annuloplasty ring.

FIGS. 2A-2E depict exemplary steps for implanting the replacement aortic valve of FIG. 1B to a tissue annulus, in which:

FIG. 2A shows the replacement aortic valve mounted on a balloon catheter and advancing into position within the aortic annulus;

FIG. 2B shows the replacement aortic valve in a desired implant position at the aortic annulus, with the balloon catheter advanced beyond the valve to displace a nose cone out of engagement with a coupling stent frame;

FIG. 2C shows the balloon on the catheter, inflated to expand and deploy the flared coupling stent frame against and below the aortic annulus;

FIG. 2D shows the deflated balloon on the catheter along with the nose cone being removed from within the valve; and FIG. 2E shows the fully implanted replacement aortic valve.

FIGS. 3A and 3B depict the step of curing the curable composition after positioning the aortic implant at its implant location, in which:

FIG. 3A depicts a probe comprising an energy source advancing towards the aortic heart valve to be positioned coaxially with either one of the sewing ring or the stent frame; and FIG. 3B depicts the energy source being contained within the balloon.

FIGS. 4A and 4B depict an exemplary method of sealing or securing the replacement aortic valve after implantation, as depicted in FIGS. 2A-2E, in which:

FIG. 4A depicts the curable composition being applied to an interface between an outflow side of the sewing ring and the aortic annulus; and FIG. 4B depicts the curable composition being cured by an energy source.

FIGS. 5A and 5B depict another exemplary method of sealing or securing the replacement aortic valve after implantation, as depicted in FIGS. 2A-2E, in which:

FIG. 5A depicts the curable composition being applied to the inflow side of the sewing ring and between the stent frame and the tissue annulus; and FIG. 5B depicts the curable composition being cured by an energy source.

FIGS. 6A-6C depict the exemplary steps for implanting an embodiment of a replacement mitral valve to a tissue annulus, in which:

FIG. 6A depicts the replacement mitral valve being guided by sutures to an implant position onto the mitral annulus;

FIG. 6B depicts the replacement mitral valve positioned on the mitral annulus and the removal of the surgical handle; and FIG. 6C depicts the removal of the mitral valve holder.

FIGS. 8A and 8B depict an exemplary method of sealing or securing the mitral valve after implantation, as depicted in FIGS. 6A-6C, in which FIG. 8A depicts the curable composition being applied to an interface between the sewing ring and the mitral annulus on the inflow side of the mitral valve; and FIG. 8B depicts the curable composition being cured by an energy source.

FIGS. 9A and 9B depict another exemplary method of sealing or securing the mitral valve after implantation, as depicted in FIGS. 6A-6C, in which:

FIG. 9A depicts the curable composition being applied to an interface between the mitral valve and the mitral annulus on the outflow side of the mitral valve; and FIG. 9B depicts the curable composition being cured by an energy source.

FIGS. 12A-12B depict an exemplary embodiment of a combined implantable heart valve delivery device and energy source that can be provided in a retracted state (FIG. 12A) for delivery and an expanded state (FIG. 12B) for implantation and sealing.

FIGS. 14A-14B depict another exemplary embodiment of a combined implantable heart valve delivery device and energy source that can be provided in a retracted state (FIG. 14A) and an expanded state (FIG. 14B).

DETAILED DESCRIPTION OF THE EXEMPLARY EMBODIMENTS

Figure 1A:
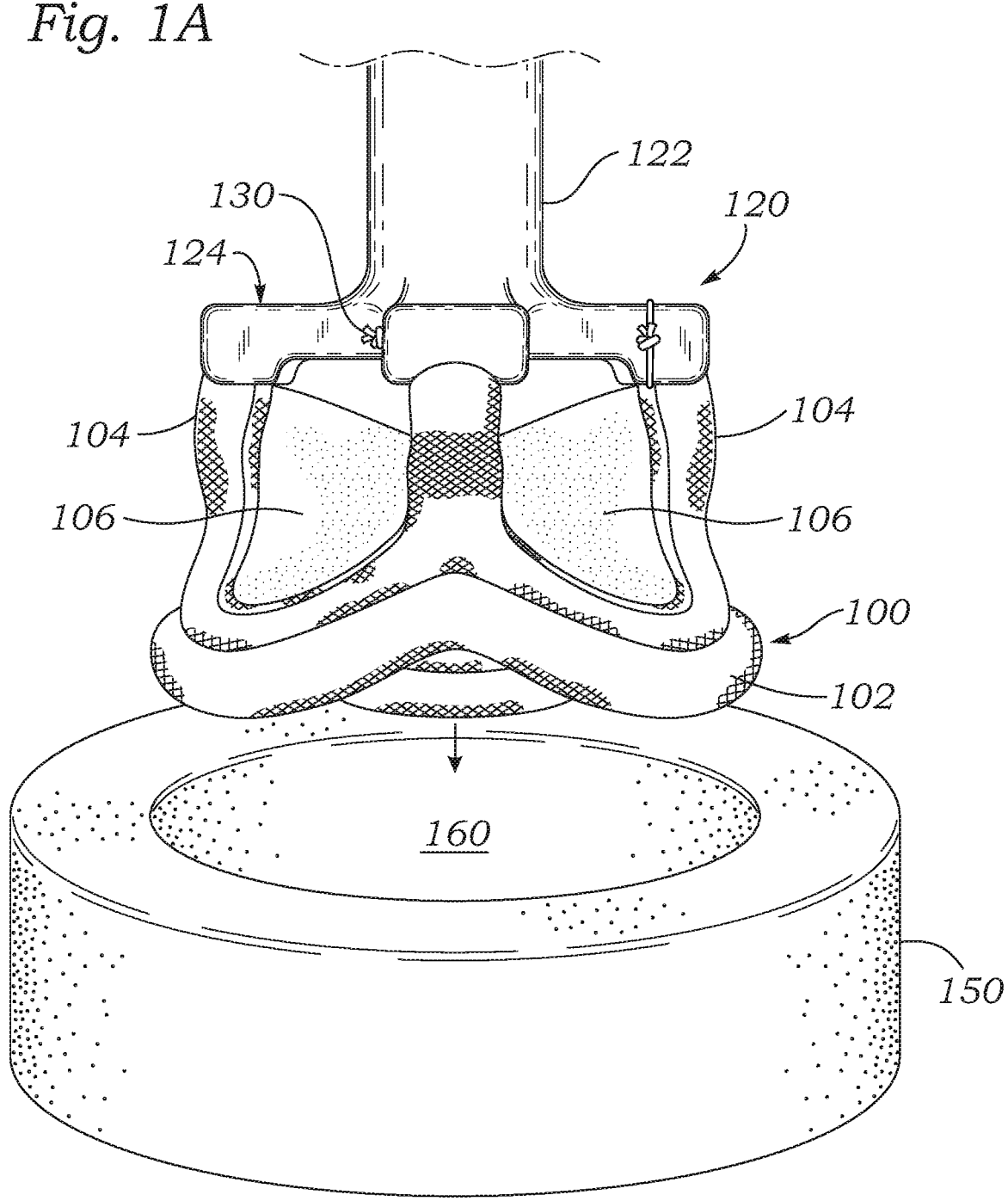

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope, and contemplation of the present invention as further defined in the appended claims. Features described with respect to one embodiment can be incorporated into other embodiments disclosed in this application.

The curable compositions disclosed herein can be used to seal and/or secure an implantable medical device to an anatomical feature in a patient's body. Among the challenges that are presented by the implantation of medical devices is the ability to effectively secure (i.e. adhere) and/or seal the device to a wet tissue or in a wet environment, such as inside a heart or a patient's vasculature.

In embodiments where the curable composition provides a seal between the implantable medical device and the anatomical feature, the curable composition can be formulated as a sealant such that it is effective in preventing fluid flow through the areas in which the sealant is applied. In one embodiment, the sealant is capable of filling a volume of space between an implantable medical device and the adjacent anatomical feature. For a bioprosthetic heart valve, for example, the sealant provides a seal between a peripheral surface, such as a sewing ring or stent of a bioprosthetic heart valve, and the tissue annulus within which the valve is implanted. The sealant desirably has the ability to maintain the required volume that is required to fill the space and thus prevent fluid flow therethrough.

The sealant can have a lower adhesive strength than would be required for an adhesive since the sealant is not relied upon to secure the implantable medical device to the anatomical feature. Rather, other securement means can be employed, such as sutures or staples, to secure the device. In one embodiment, the sealant can have a sufficient adhesive strength that permits it to remain at the site of application and resist being displaced by the typical forces that can act upon it. In embodiments where the sealant is being used to provide a seal between a medical implant device, e.g., a bioprosthetic heart valve, and a tissue within a heart, the sealant can preferably have sufficient adhesive strength and durability to withstand the hemodynamic and pulsatile forces of the heart.

Separately or in addition, in embodiments where the curable composition secures the implantable device to an anatomical feature, the curable composition can be formulated as an adhesive such that it provides sufficient adhesive strength to maintain the implantable medical device at a desired implant location. In one embodiment, the adhesive can obviate the need for sutures or other securement methods such that the implantable medical device is secured to the anatomical feature using only the adhesive. Thus, in accordance with this embodiment, the adhesive is understood to have a higher adhesive strength than a sealant. It is understood, however, that in certain embodiments, the adhesive can also serve to provide a seal between the implantable medical device and the tissue and can therefore be considered both an adhesive and a sealant. In one embodiment, sutures and/or other securement methods can be used in combination with the adhesive.

The implant devices/implantable medical devices disclosed herein can be any bioprosthetic device that can be implanted in a patient, whether through surgical, minimally-invasive, or percutaneous methods. Exemplary implantable medical devices include bioprosthetic heart valves, including surgical, transcatheter, aortic, and mitral heart valves. Another exemplary implantable device that can incorporate the curable composition for securement to the tissue can be an annuloplasty ring. Other implantable devices that can incorporate the curable composition for securement to the tissue can be stents, grafts, combination devices, valves for implantation in other valve areas, and other implants.

For bioprosthetic heart valves, it is desirable for the implanted heart valve to form a seal with the surrounding tissue annulus at the site of implantation such that blood does not flow between the heart valve and the tissue wall (a complication known as perivalvular leakage or PVL) but flows only through the central flow orifice of the heart valve. It is also desirable to be able to secure the bioprosthetic heart valve without the need for sutures or other additional securement means, which can be time-consuming.

To that end, the bioprosthetic heart valves can be configured such that a curable composition can be applied to portions of the heart valves adjacent to or in direct contact with the tissue annulus. The curable composition can also be applied to the interface, which includes both the portion of the heart valve and the adjacent tissue annulus.

The anatomical feature to which the implantable medical device can be sealed or adhered to can include the valve annuli of the heart, including the aortic valve annulus, the mitral valve annulus, pulmonary valve annulus, and the tricuspid valve annulus. While the exemplary embodiments disclosed herein describe the adhesion or sealing of a bioprosthetic heart valve to a valve annulus, it is understood that the anatomical feature can also include any tissue substrate (e.g., to various tissue areas in the vasculature or other areas) within a patient to which it is desired to adhere or seal an implantable medical device. In one embodiment, the curable composition can be applied directly to the anatomical feature or tissue, the implantable medical device, or both prior to implantation of the implantable medical device.

Figure 1B:
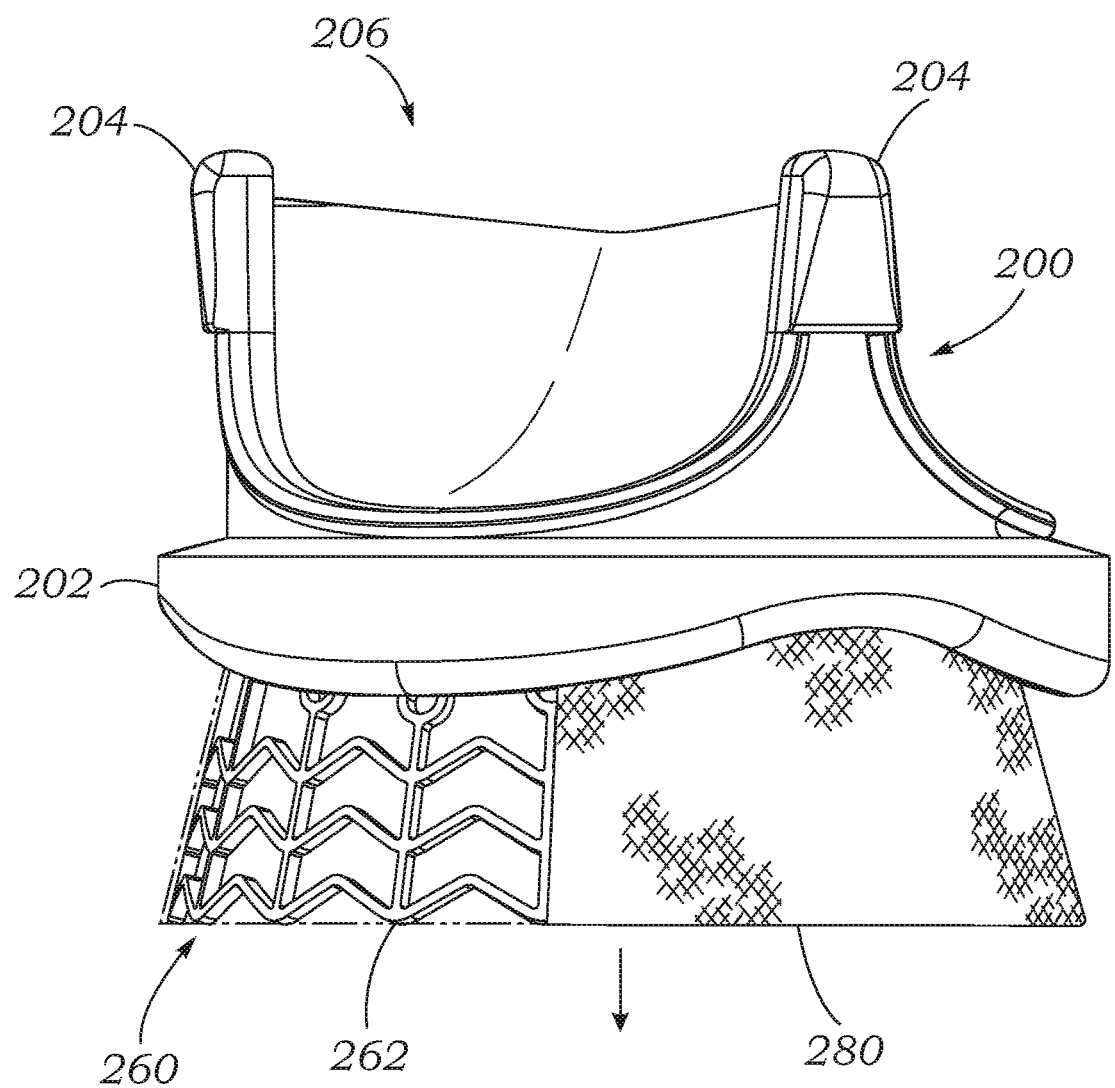

FIGS. 1A and 1B depict exemplary embodiments of surgical valves that can be used in connection with the curable compositions and methods disclosed herein.

FIG. 1A depicts an embodiment of an exemplary replacement aortic valve 100 attached to an aortic valve holder 120. The aortic valve 100 can comprise an inflow sewing ring 102 and a plurality of commissure posts 104 extending away from the sewing ring 102. A tissue valve leaflet structure 106 can be coupled to the commissure posts 104. The aortic valve 100 is depicted as being attached to an aortic valve holder 120 at its outflow end via the commissure posts 104. The aortic valve holder 120 can include a central hub 122 for receiving a handle (not shown) and legs 124 coupled by sutures 130 to the commissure posts 104.

An applicator 150 can be separately provided. The applicator 150 has interior sidewalls 160 that define the central orifice. The sidewalls 160 can comprise the curable composition. The sidewalls 160 of the applicator 150 can be and are depicted in FIG. 1A as being configured to selectively contact the outer periphery of the sewing ring 102 when the aortic valve 100 is lowered into the central orifice, and the sewing ring 102 contacts the sidewalls 160 that comprise the curable composition. The sidewalls 160 can be made of a permeable material, such as a sponge, that retains the curable composition and that can transfer the curable composition onto the sewing ring 102 and/or other portions of the aortic valve 100. The sidewalls 160 of the central orifice can thus be shaped to correspond to the external contours of the sewing ring 102 and/or other portions of the aortic valve. The application of the curable composition onto the sewing ring 102 can be performed during manufacture, prior to packaging, or just prior to implantation of the aortic valve 100 into a patient (e.g., by a medical professional operating on the patient).

Once implanted, the curable composition can be located between the external periphery of the sewing ring 102 and the tissue annulus. In order to permit the transmittance of energy through the sewing ring, such as visible or UV light, to cure the curable composition, the light transmittance through the inflow sewing ring can be at least 5%, at least 10%, at least 20%, at least 30%, at least 40%, at least 50%, at least 60%, at least 70%, at least 80%, at least 90% or 100%. In another embodiment, the light transmittance can be provided within a range between and including any two of the foregoing values.

FIG. 1B depicts another exemplary embodiment of a replacement aortic valve 200. As with the replacement aortic valve 100 in FIG. 1A, the replacement aortic valve 200 in FIG. 1B can comprise an inflow sewing ring 202 and a plurality of commissure posts 204 extending away from the sewing ring 202. A tissue valve structure 206 can be coupled to the commissure posts 204. The replacement aortic valve 200 can further comprise an anchoring skirt 260 that is attached to the sewing ring 202. The anchoring skirt 260 can comprise a stent frame 262. The stent frame 262 can be delivered in a compressed configuration to provide a smaller delivery profile and expanded to an expanded configuration via a balloon catheter once the aortic valve 200 is placed at the site of implantation. The anchoring skirt 260 is depicted in FIG. 1B in the expanded configuration. The anchoring skirt 260 can also include a cover 280 (e.g., a transparent, porous, and/or woven (e.g., open weave) cloth or material) that covers all or a portion of the stent frame 262. Exemplary replacement aortic valves are described in U.S. Pat. No. 8,641,757, issued Feb. 4, 2014, the entire contents of which are incorporated herein by reference in its entirety.

The curable composition can be applied to the external surface of the sewing ring 202, anchoring skirt 260, stent frame 262, the cover 280, the commissure supports 204, another location, and/or a combination of these as desired and/or depending on the specific configuration of the aortic valve 200. The application of the curable composition can be accomplished in a similar manner as described with respect to FIG. 1A, by the provision of an applicator having a suitably shaped sidewall and/or in other ways. For example, the application of the curable can also be performed by applying, brushing or injecting the curable composition directly onto the desired areas of the sewing ring 202 and anchoring skirt 260. Optionally, and as depicted in FIGS. 4 and 5, the curable composition can be applied to the aortic valve 200 and/or surrounding native tissue in vivo after implantation of the aortic valve 200.

The cover or porous or open weave cloth 280 can be configured such that energy, particularly visible or UV light, can be transmitted through the cover/cloth 280 and cure the curable composition disposed between the cover/cloth 280 and the tissue. The light transmittance through the cover/cloth 280 can be at least 5%, at least 10%, at least 20%, at least 30%, at least 40%, at least 50%, at least 60%, at least 70%, at least 80%, at least 90% or 100%. In another embodiment, the light transmittance can be provided within a range between and including any two of the foregoing values.

FIGS. 1C, 1D, 1E, and 1F depict some exemplary embodiments of transcatheter prosthetic heart valves that can be used in connection with the curable compositions and methods described herein.

Figure 1C:
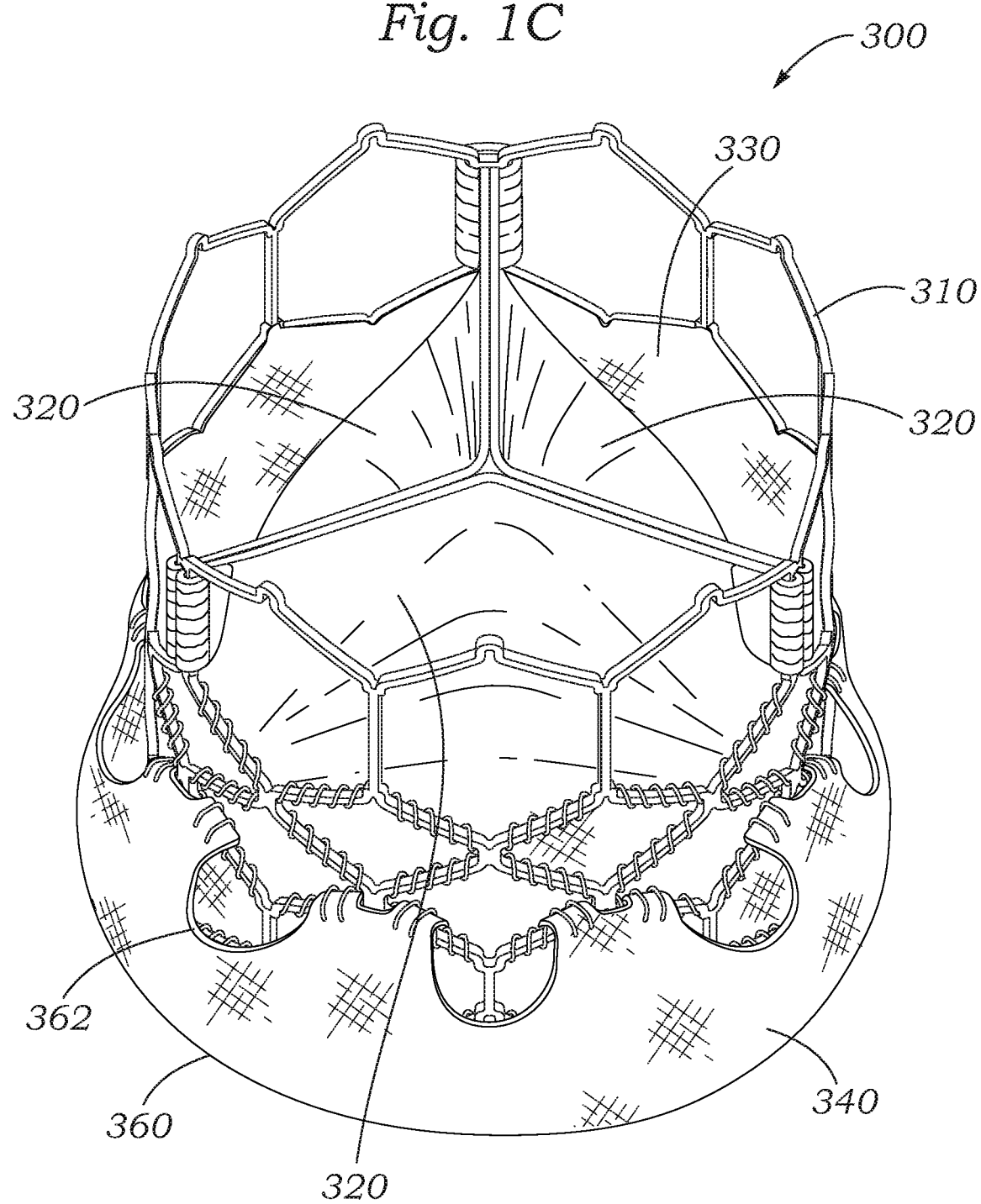

FIG. 1C depicts an embodiment of a transcatheter prosthetic heart valve 300 that is adapted to be implanted in an aortic annulus, although it can be adapted to be implanted in other native annuluses of the heart. The heart valve 300 can have four main components: a stent or frame 310, a valvular structure 320, an inner skirt 330, and an outer skirt 340. Exemplary transcatheter heart valves are described in U.S. Patent Application Publication No. 2012/0123529, published on May 17, 2012, the entire contents of which are incorporated herein by reference in its entirety.

The transcatheter heart valve 300 can be delivered in a radially compressed state through the vasculature of a patient. Once the heart valve 300 reaches its intended site of implantation, the heart valve 300 can be radially expanded, as shown in FIG. 1C.

The curable compositions described herein can be applied directly to the outer skirt 340 of the heart valve 300. In addition to providing a seal between the heart valve 300 and the tissue annulus to mitigate the occurrence of PVL, the outer skirt 340 can be secured to the frame 310 such that when the frame 310 is in the expanded state, there is excess material or slack between the outer skirt's lower and upper edges 360, 362 that does not lie flat against the outer surface of the frame 310. In one embodiment, the outer skirt 340 can be configured with excess material which causes the outer skirt 340 to bulge outwardly as the frame shortens in length during radial expansion. Accordingly, when the valve 300 is deployed within the native annulus, the excess material of the outer skirt 340 can fill in gaps between the frame 310 and the surrounding tissue annulus. The outer skirt 340 therefore can cooperate with the inner skirt 330 to avoid PVL after implantation of the valve 300.

Again, the inner skirt 330 and outer skirt 340 can provide a light transmittance of at least 5%, at least 10%, at least 20%, at least 30%, at least 40%, at least 50%, at least 60%, at least 70%, at least 80%, at least 90% or 100%. In another embodiment, the light transmittance can be provided within a range between and including any two of the foregoing values.

Figure 1D:
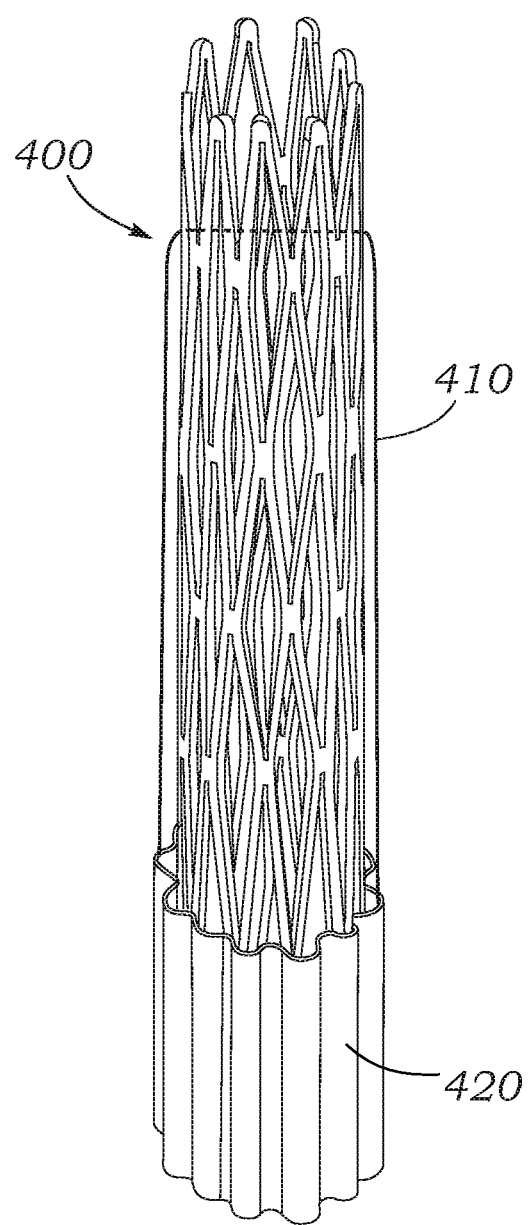
Figure 1E:
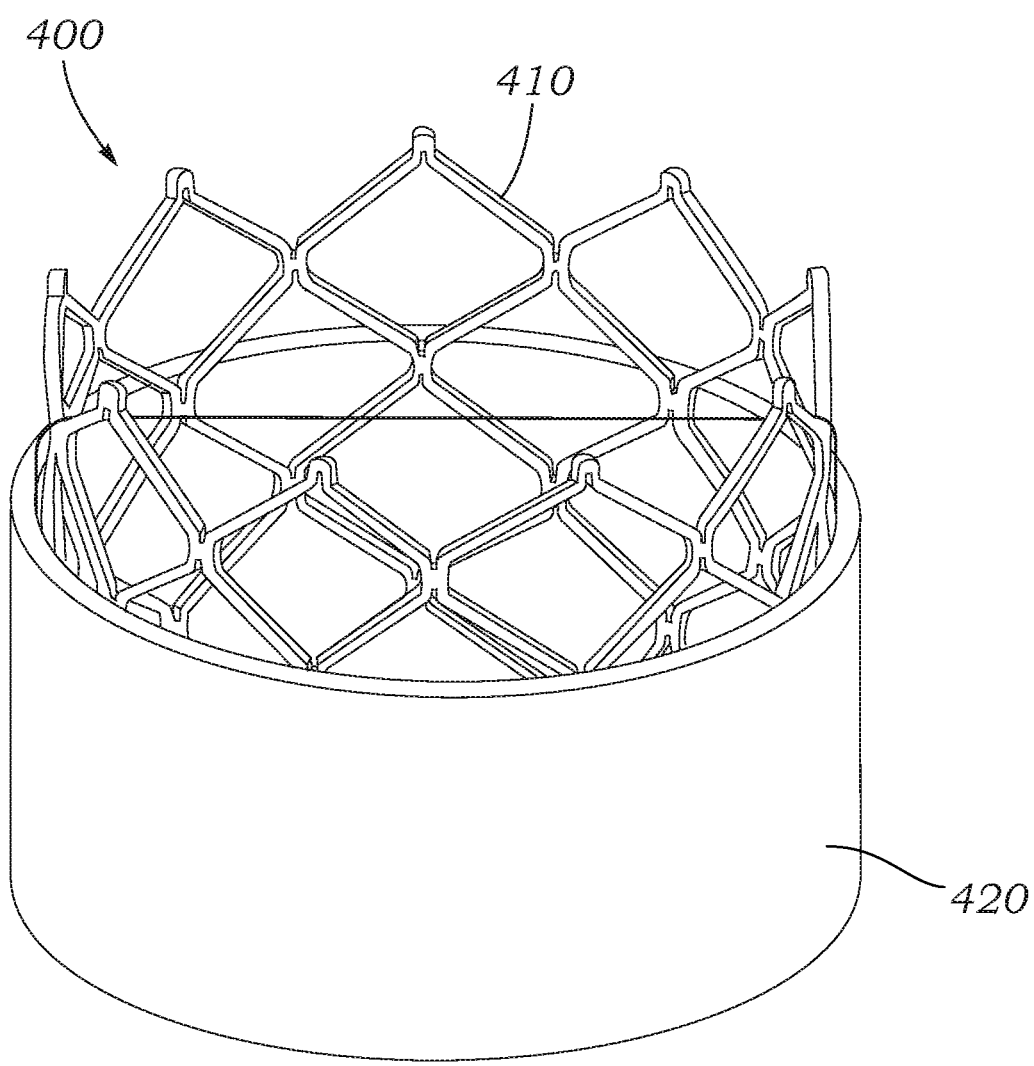

FIGS. 1D and 1E depict an embodiment of a transcatheter heart valve 400 in the compressed state/configuration (FIG. 1D) and the expanded state/configuration (FIG. 1E). Exemplary transcatheter heart valves are described in U.S. Pat. No. 8,795,357, issued Aug. 5, 2014, the entire contents of which are incorporated herein by reference in its entirety. The heart valve 400 is generally depicted as including a frame or stent 410 and a sealing device 420 mounted to the frame. The heart valve 400 can also include a valvular leaflet structure (not shown, but can be the same as or similar to leaflet structures described or shown elsewhere herein of otherwise known) mounted or sutured to the frame 410. The sealing device 420 can be applied onto and/or form part of an annular skirt (e.g., which can be the same as or similar to other annular skirts described or shown herein or otherwise known). The annular skirt and/or the sealing device 420 can be positioned inside or outside of the frame 410. The sealing device 420 can be operatively connected to the frame 410 in such a manner that radial expansion of the heart valve 400 causes the sealing device 420 to be mounted or deployed from its delivery configuration (FIG. 1D) to its operational or functional orientation/configuration (FIG. 1E).

The curable compositions described herein can be applied directly to the sealing device 420 either when it is in the compressed state/configuration as shown in FIG. 1D or in its expanded state as shown in FIG. 1E (e.g., prior to compression or after expansion). The sealing device 420 can be formed in a variety of ways and with a variety of materials. For example, the sealing device 420 can be made of a thin, flexible sheet of material and can be made of any various suitable materials, such as a fabric, PET, PTFE, ePTFE, ultra-high molecular weight polyethylene UHMWPE, tissue, metal, sponge or a polymer. The seating device can either be transparent, porous or provided as a porous or woven fabric that permits the transmittance of light therethrough. Again, the sealing device 420 can provide a light transmittance of at least 5%, at least 10%, at least 20%, at least 30%, at least 40%, at least 50%, at least 60%, at least 70%, at least 80%, at least 90%, or 100%. In another embodiment, the light transmittance can be provided within a range between and including any two of the foregoing values.

Figure 1F:
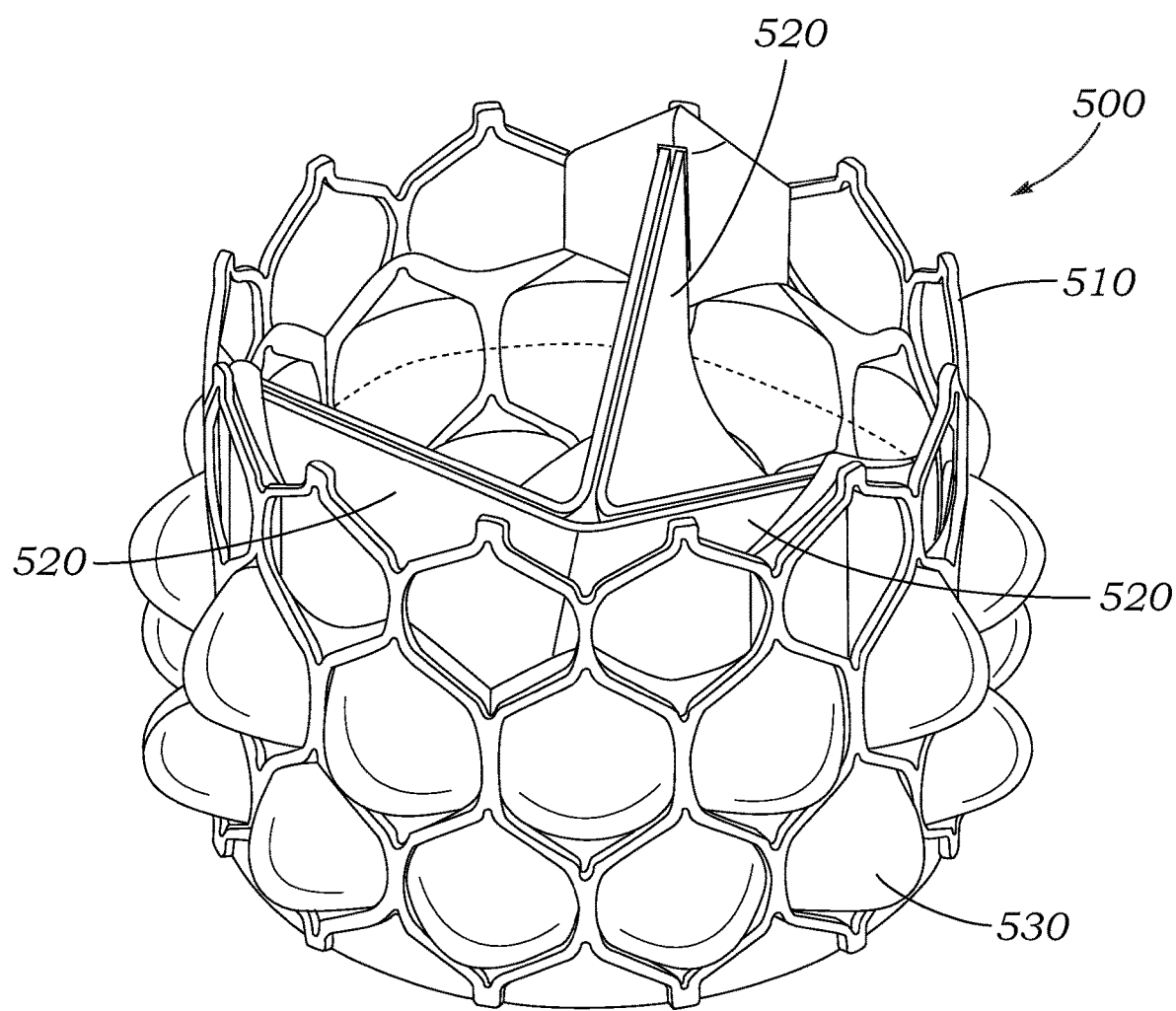

FIG. 1F depicts an exemplary embodiment of a transcatheter prosthetic heart valve 500 including a frame or stent 510 and a leaflet structure comprising a plurality of leaflets 520. The heart valve 500 can include a sealing device or skirt 530 (e.g., which can be the similar to other sealing devices or skirts described elsewhere herein or otherwise known). The frame 510 can be made from any suitable self-expandable or plastically-expandable materials known in the art. The skirt 530 is shown in FIG. 1F as being positioned on the inside of the frame 510 and the skirt 530 can be made of any various suitable materials, such as a fabric, PET, PTFE, ePTFE, ultra-high molecular weight polyethylene UHMWPE, tissue, metal, sponge, or a polymer. As shown in FIG. 1F, at least during ventricular diastole (when the leaflets of the prosthetic valve are closed) or at all times, the excess skirt material 530 can protrude outwardly through the openings in the frame 510, as shown, and can contact tissue surrounding the valve to help seal the area between the frame and the surrounding tissue. For example, during ventricular diastole, the pressure gradient across the valve 500 can cause the excess skirt material 530 to protrude outwardly through the openings in the frame 510 and contact tissue surrounding the valve. The curable composition described herein can be applied to one or more of various portions of heart valve 500. For example, the curable composition can be applied to those portions of the skirt 530 protruding outwardly through the openings in the frame 510 to couple to the adjacent tissue annulus.

Figure 1G:
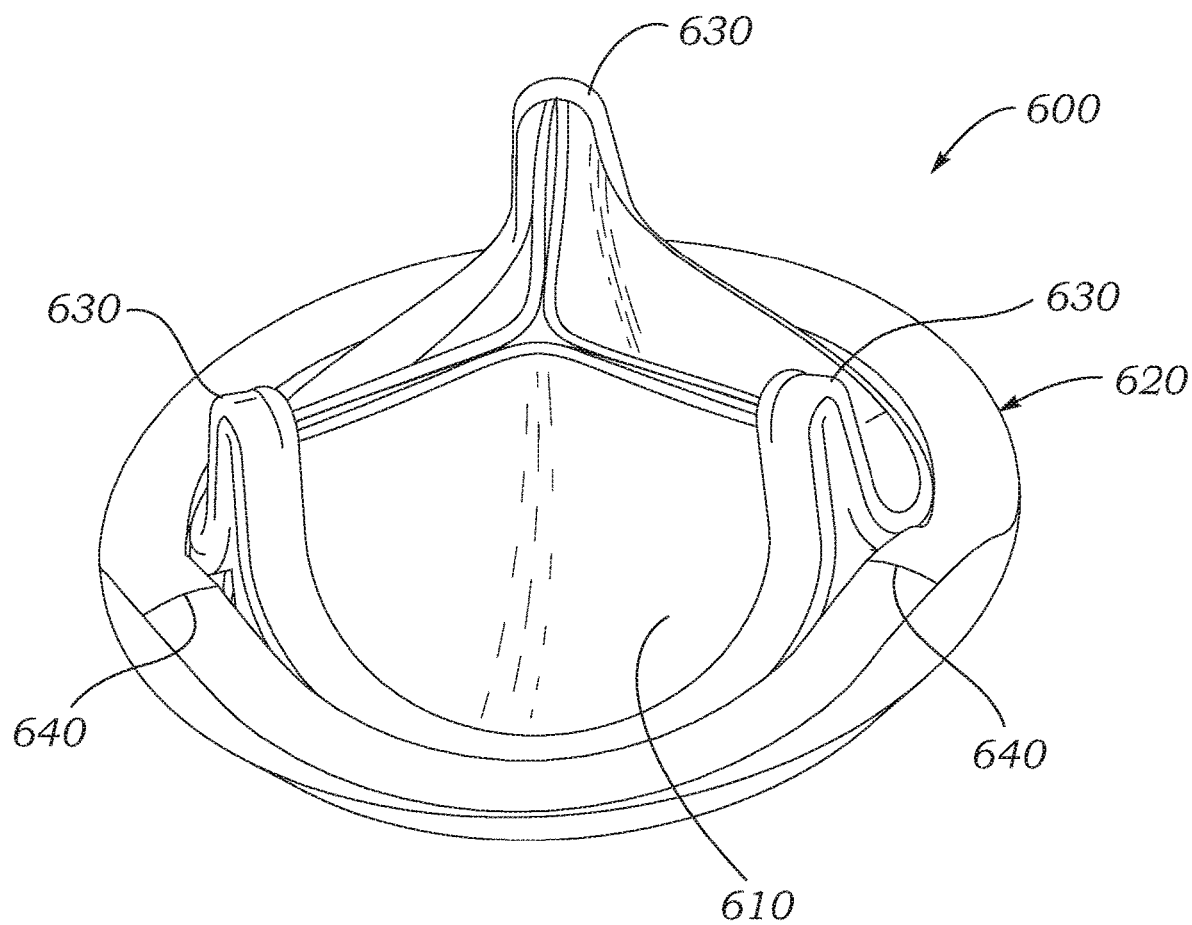

FIG. 1G depicts an exemplary embodiment of a mitral valve 600 comprising a flexible tissue valve and having a sewing ring 620 at the inflow end and a plurality of commissure posts 630 that support the leaflets of the tissue valve. The mitral valve 600 is intended for implant in the mitral annulus between the left atrium and the left ventricle, though it could be implanted in other native valve annuluses or locations. The sewing ring 620 is further provided with optional markers 640 to indicate proper orientation. Exemplary embodiments of the mitral valve are described in U.S. Pat. No. 6,966,925, issued on Nov. 22, 2005, the entire contents of which are incorporated herein by reference in its entirety.

Figure 6A:
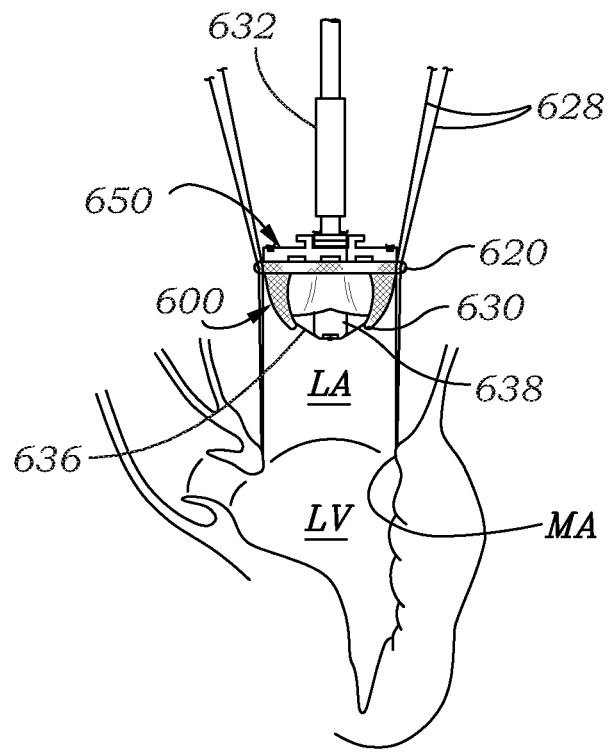
Figure 6B:
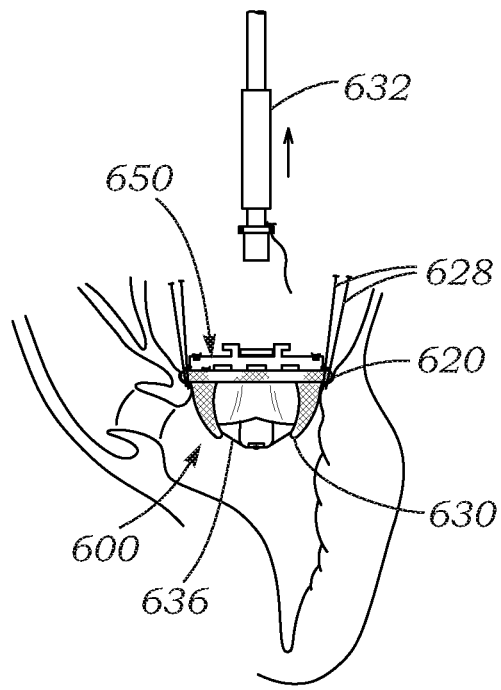
Figure 6C:
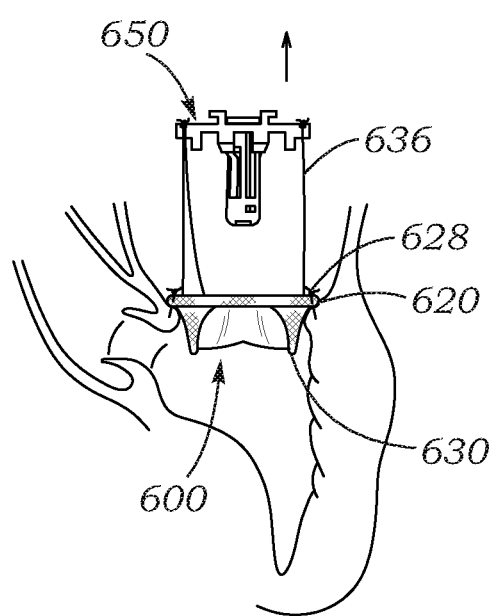

The curable composition can be applied to the external surface of the sewing ring 620 and/or other locations. The application of the curable composition can be accomplished in a similar manner as described with respect to FIG. 1A, by the provision of an applicator having a suitably shaped sidewall or in any other ways disclosed herein. The application of the curable composition can also be performed by applying, brushing, or injecting the curable composition directly onto the desired areas of the sewing ring 620. Optionally, and as depicted in FIGS. 6A-6C, the curable composition can be applied in vivo after implantation of the mitral valve 600.

Figure 1H:
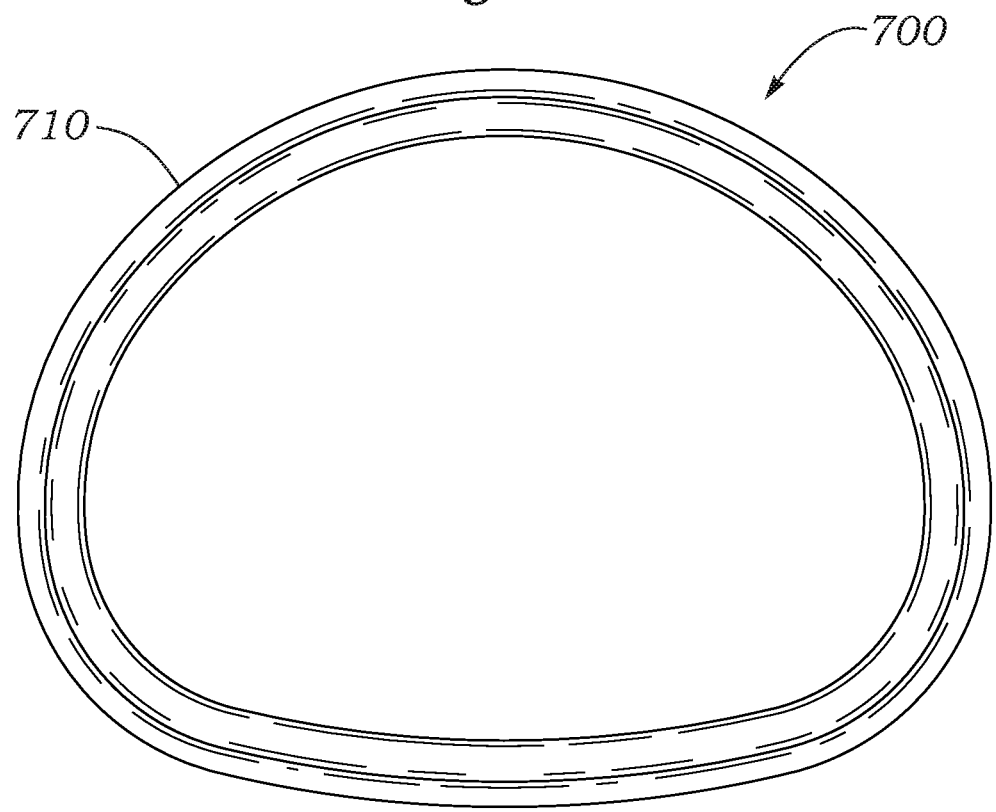
Figure 1I:
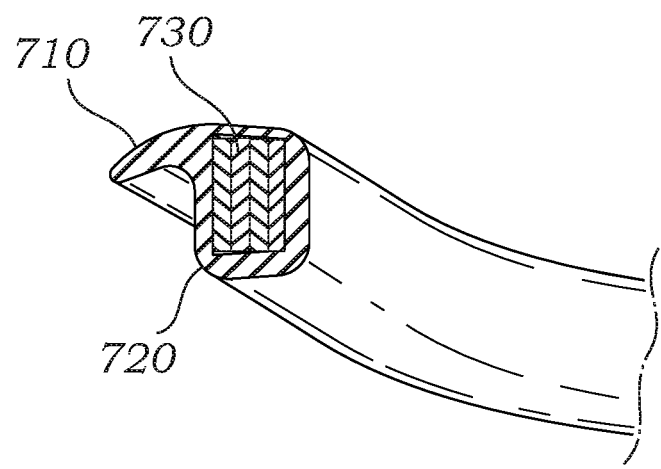

FIGS. 1H and 1I depict an exemplary embodiment of an annuloplasty ring 700 that comprises a radially outwardly extending sewing margin 710. As further shown in FIG. 1I, an outer cover 720 can closely surround a core 730 and can desirably include a radially outwardly extending sewing margin 710. The core 730 can include a plurality of concentric bands. The core 730 can be formed from a solid member. In one optional embodiment, the outer cover 720 can be made of a transparent, porous, and/or woven material that permits the transmittance of light therethrough. Optionally, the core 730 can be made of a transparent, porous, and/or woven (e.g., open weave or braided) material that also permits the transmittance of light therethrough. Exemplary embodiments of the annuloplasty ring are described in U.S. Pat. No. 8,152,844, issued on Apr. 10, 2012, the entire contents of which are incorporated herein by reference in its entirety.

The curable composition can be applied to one or more of a variety of location on ring 700. For example, the curable composition can be applied to the outer cover 720 or a portion thereof, e.g., to the radially outwardly extending sewing margin 710. The application of the curable composition can be accomplished in a similar manner as described with respect to FIG. 1A, by the provision of an applicator having a suitably shaped sidewall, or in any other way disclosed elsewhere herein. For example, the application of the curable composition can also be performed by applying, brushing or injecting the curable composition directly onto the desired areas of the outer cover 720, e.g., to the sewing margin 710. Optionally, the curable composition can be applied in vivo after implantation of the annuloplasty ring 700 in a similar manner as depicted in FIGS. 8 and 9.

Figure 10:
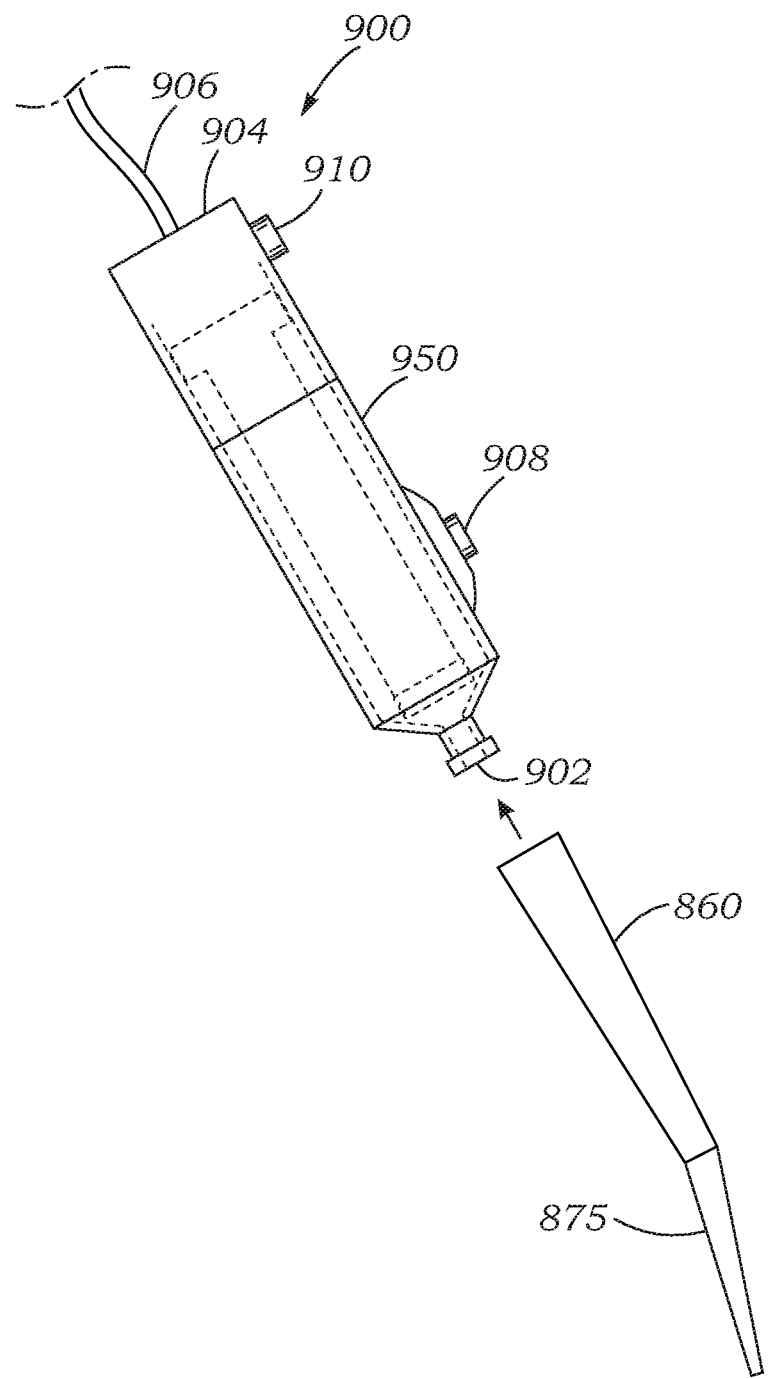
FIG. 10 depicts an embodiment of an applicator and extrusion tip that can be used to deliver the curable composition to a desired location in a patient's body, on an implantable medical device, or at the interface between the implantable medical device and an anatomical feature.

An exemplary embodiment of an applicator and exemplary embodiments of extrusion tips that can be used to deliver the curable composition are depicted in FIGS. 10 and 11A-C. FIG. 10 depicts an exemplary applicator 900 that is coupled at one end 904 to a source of compressed air via connector 906. A power button 908 can be actuated in an on/off position to control the generation of compressed air through the connector 906 and into an internal cavity of the applicator 900. The internal cavity can also house a cartridge 950 that contains the curable composition. In one embodiment, the cartridge 950 can comprise a single chamber that contains the curable composition. In one embodiment, the cartridge 950 can comprise two chambers to separately contain a pre-polymer and an initiator of the curable composition. An extrusion tip 860 can be fitted to an end orifice 902 of the applicator 900.

Once the source of compressed air is turned on via the power button 908, a pressure regulator 910 can be used to regulate the amount of pressure applied to the cartridge 950 to extrude the curable composition out of the end orifice 902 and through the extrusion tip 860. In one embodiment, the extrusion tip can have an angled end 875 to more easily enable approach and placement of the tip at a desired site of application within a relative narrow area, such as the aortic or mitral annulus of a patient's heart.

Figure 5A:
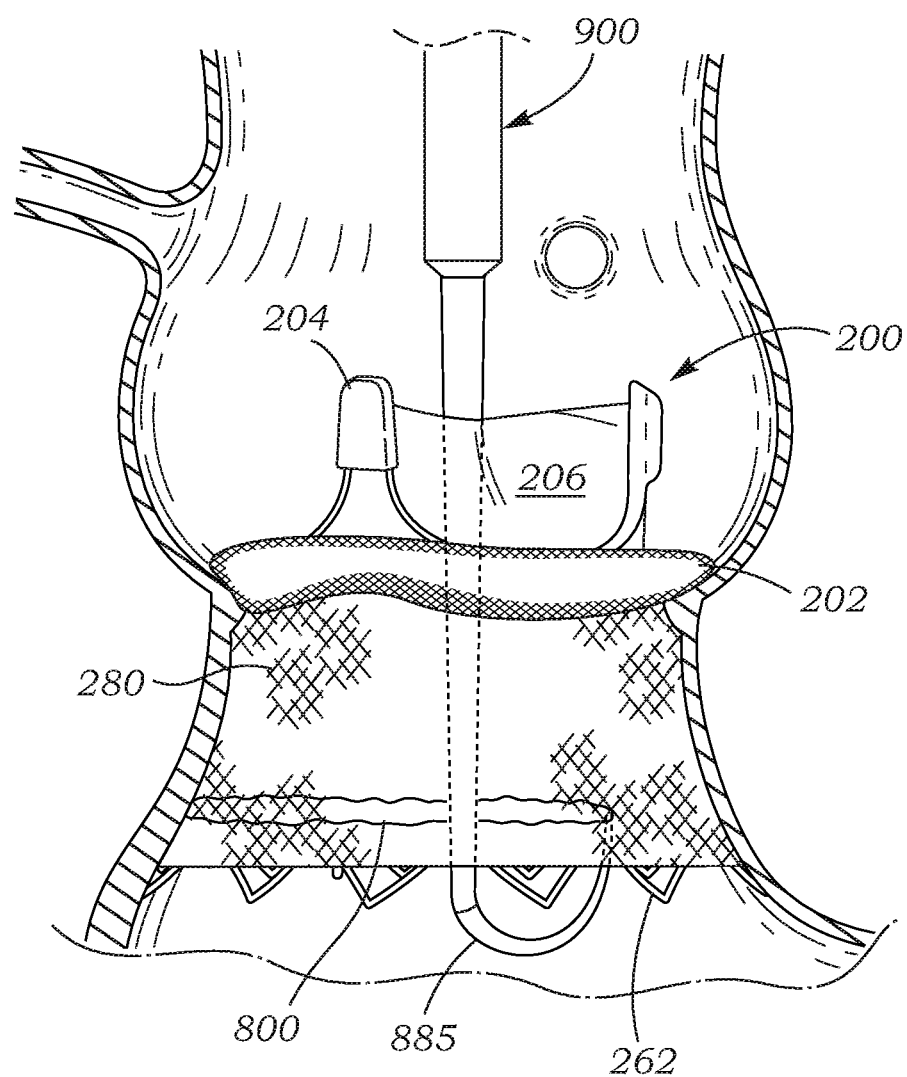
Figure 9A:
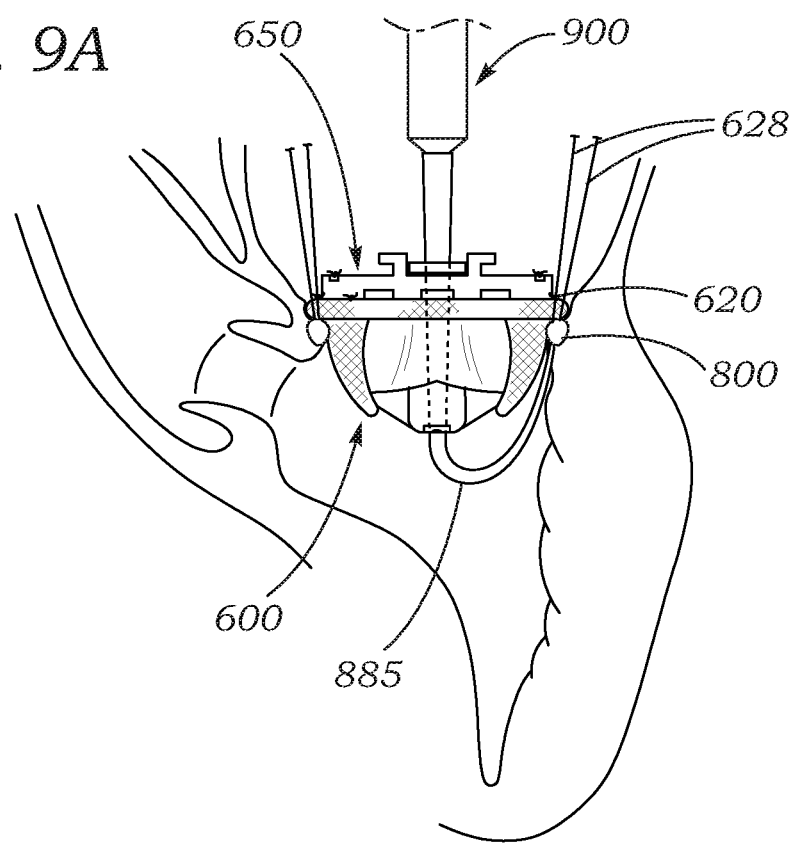

A variety of different extrusion tips can be provided to accommodate a patient's unique anatomy (e.g., these can be provided individually or in a kit or set of multiple tips) and to accommodate different approaches to application. For example, the extrusion tip can have a hooked end 885, as depicted in FIGS. 5A and 9A to enable application of the curable composition on a side of the implantable medical device that can be distal to the surgeon or the operator as shown in, for example, FIGS. 5A-5B and 9A-9B.

Figure 11A:
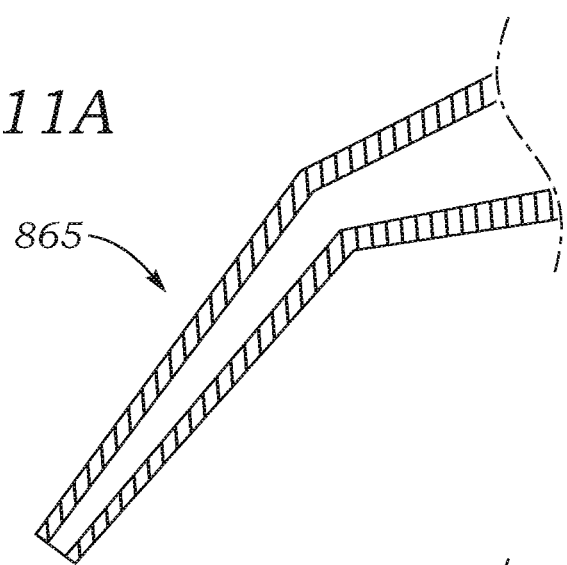
FIGS. 11A-11C depict optional embodiments of extrusion tips that can be used with the applicator depicted in FIG. 10.
Figure 11B:
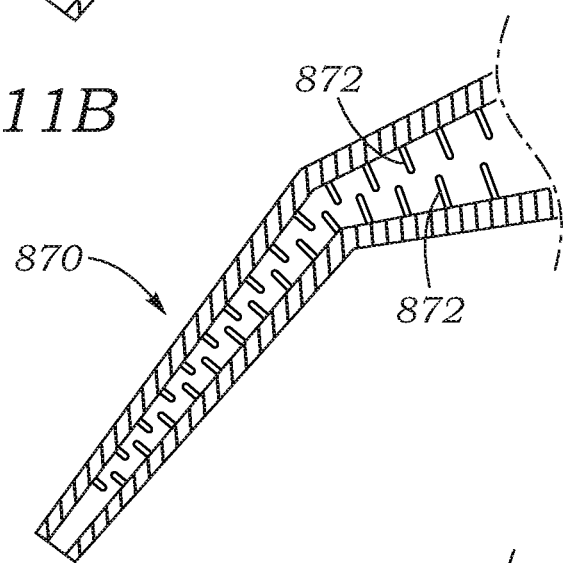
Figure 11C:
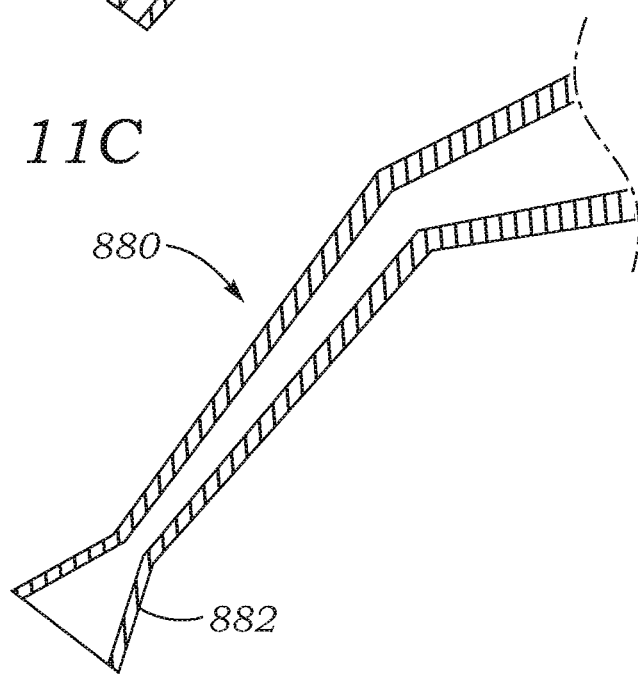

FIG. 11A-11C are cross-sectional views of different exemplary extrusion tips, with FIGS. 11A and 11B depicting embodiments of extrusion tips similar to the extrusion tip 860 depicted in FIG. 10. FIG. 11A depicts an extrusion tip 865 that can be suitable in embodiments in which the curable composition is contained within a single chamber of the cartridge 950. FIG. 11B depicts an extrusion tip 870 that comprises a plurality of opposing vanes 872 that permit mixing of two or more components as it is extruded through the extrusion tip 870. The extrusion tip 870 is particularly suitable for embodiments in which the curable composition comprises two or more components that are housed in separate chambers of the cartridge 950. Another example could include two or more lumens such that components of the curable composition do not mix until the lumens combine or deposit the components out of the end of the tip. FIG. 11C depicts an extrusion tip 880 having a flared tip 882 that permits a larger volume of the curable composition to be applied to the desired location.

Some applicators can be designed to application of the curable composition via a transcatheter procedure. One or more portions of the applicator (e.g., the cartridge 950, power button 908, etc.) can be remote from an extrusion catheter or tip for operation outside a patient's body, while the applicator end is positioned in desired location inside the body to apply the curable composition. For example, an applicator can be configured or at least partially configured as a steerable catheter that can be directed to the desired location.

FIG. 2A-2E are sectional views through an isolated aortic annulus AA showing a portion of the adjacent left ventricle and ascending aorta with the sinus cavities.

Figure 2A:
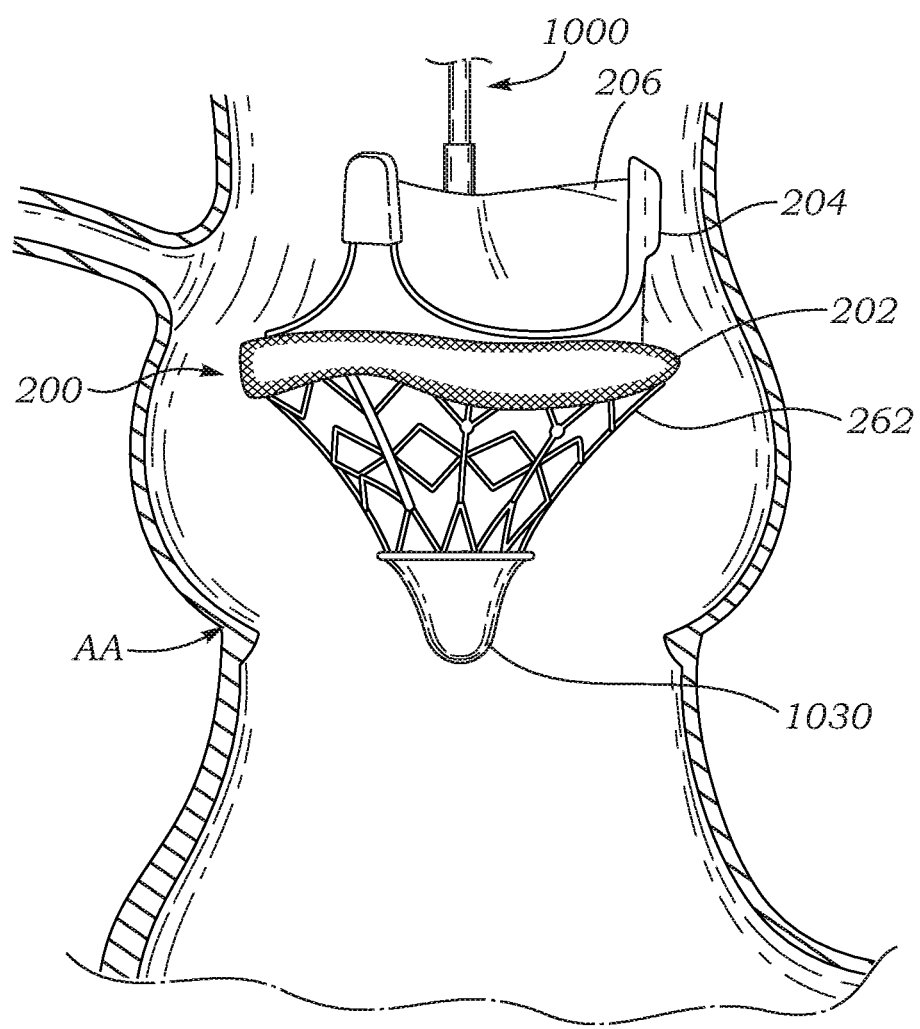

FIG. 2A shows a prosthetic aortic valve 200 mounted on a balloon catheter 1000 having a balloon in a deflated state near a distal end and advancing into position so that it is approximately axially centered at the aortic annulus AA. Balloon catheter 1000 can include a balloon 1020 proximate a distal end of the balloon catheter 1000. In 2A and 2B, the balloon 1020 is in a deflated state. The aortic valve 200 shown in 2A-2E can be the same as or similar to the aortic valve 200 as depicted in FIG. 1B and described above. The anchoring skirt 260 and/or stent frame 262 can take on a conical shape that is tapered at the nose cone 1030 in the radially constricted or undeployed state as depicted in FIGS. 2A and 2B. The catheter 1000 extends through the aortic valve 200 and terminates in the distal nose cone 1030.

FIG. 2B depicts the aortic valve 200 advanced to its desired implant position at the aortic annulus AA. The sewing ring or suture-permeable ring 202 is depicted as abutting the aortic annulus AA. The balloon catheter 1000 has advanced relative to the aortic valve 200 to displace the nose cone 1030 out of engagement with the stent frame 262. A dilation balloon 1020 can be seen just beyond the distal end of the stent frame 262.

FIG. 2C shows the balloon 1020 on the balloon catheter 1000 being inflated to expand and deploy the anchoring skirt 260 and/or stent frame 262 against the annulus. The balloon 1020 is desirably inflated using controlled, pressurized, sterile physiologic saline. The anchoring skirt 260 and/or stent frame 262 transitions between its conical contracted state and an expanded, more tubular shape. The interference between the anchoring skirt 260 and/or stent frame 262 and the annulus can alone be sufficient to anchor the aortic valve 200 or interacting/anchoring features such as projections, hooks, barbs, or fabric, to name a few, can also be utilized. In one embodiment, the anchoring skirt 260 can comprise a plastically-expandable cloth-covered stainless-steel tubular stent, as depicted in FIG. 1B.

FIG. 2D shows the deflated balloon 1020 on the balloon catheter 1000 along with the nose cone 1030 being removed from within the aortic valve 200.

FIG. 2E shows the fully deployed aortic valve 200 coupled to the aortic annulus AA.

The curable compositions can be utilized to help secure or seal the aortic valve 200 in the position as shown in FIG. 2E. This can be accomplished in a number of different methods. For example, in one embodiment, the curable composition can be applied directly onto the aortic annulus and/or other tissue prior to the introduction of the aortic valve 200 and its associated balloon catheter 1000. An applicator (e.g., applicator 900 as depicted in FIG. 10, etc.) can be used to extrude the curable composition, e.g., through a pre-selected extrusion tip, such as for example, extrusion tips 860, 865, 870 and 880 as depicted in FIGS. 11A-11C or another type of tip/catheter.

Optionally, the curable composition can be applied to aortic valve 200 at the peripheral surface of the sewing ring 202, skirt 260, stent frame 262, and/or or the cover 280, just prior to the introduction of the aortic valve 200 into the patient's body using an applicator (e.g., the applicator depicted in FIG. 1A, the applicator and tips depicted in FIGS. 10 and 11A-11C, and/or another applicator.

An energy source that effectively cures the curable composition can be applied after implantation, e.g., as depicted in FIGS. 3A, 3B, 4A, 4B, 5A, 5B, 7, 8B, 9B. This can be done whether the curable composition is applied directly on to the aortic annulus, on the aortic valve 200, or elsewhere.

Figure 3A:
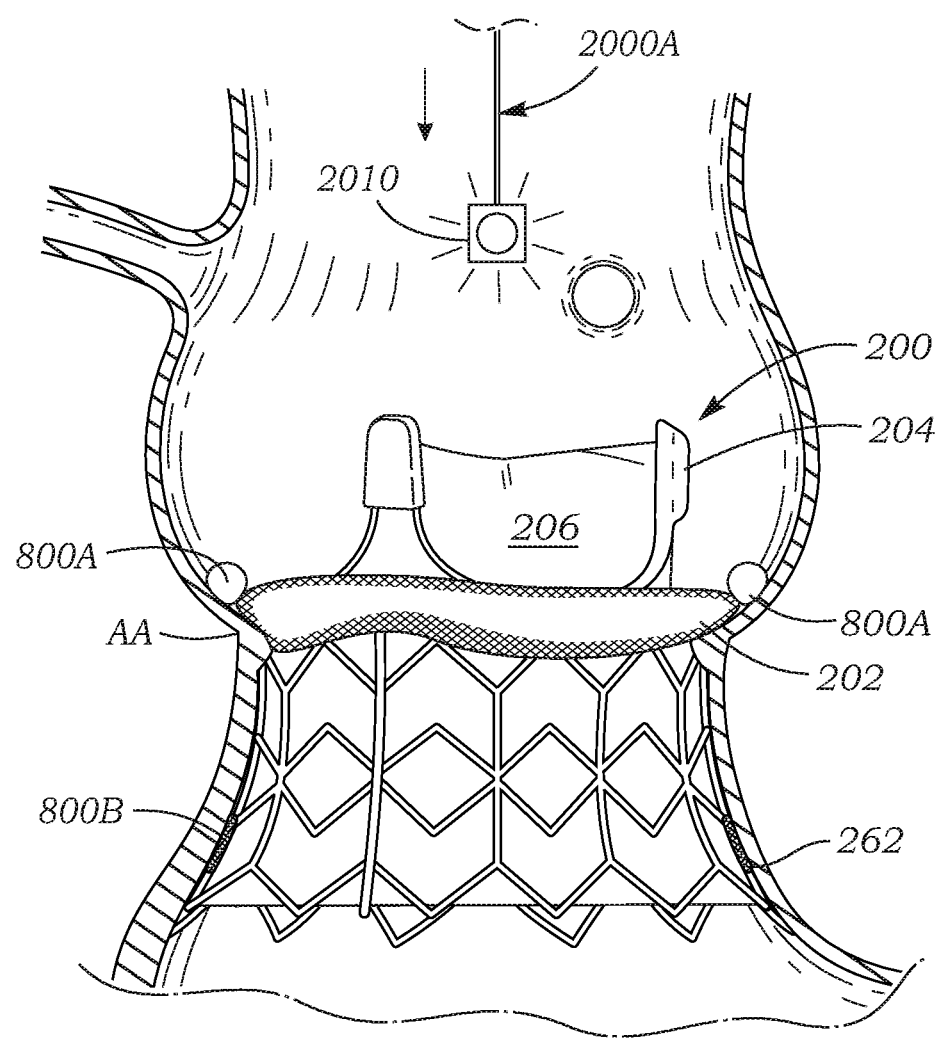

FIG. 3A depicts a probe 2000A that comprises an energy source 2010 effective to cure the curable composition. In one embodiment, the energy source 2010 can be electromagnetic radiation and/or thermal energy, which is provided at the end of an elongated shaft. The elongated shaft can be one or more of rigid, semi-rigid, pliable, flexible, etc. at various locations along its length so as to enable it to be shaped in a manner that will allow it to be positioned near the location in which the curable composition is applied. In the embodiment depicted in FIG. 3A, the curable adhesive is provided between the sewing ring 202 and the aortic annulus at 800A and/or between the skirt 260/stent frame 262 and the tissue wall at 800B. The energy source 2010 can be advanced inside the aortic valve 200 and positioned adjacent the sewing ring 202 or the skirt 260/stent frame 262 to apply curing energy to the curable composition 800. The sewing ring 202 and the skirt 260/stent frame 262 can be constructed of a material that permits the transmission of an effective amount of the energy (e.g., electromagnetic radiation, ultraviolet light, thermal energy, etc.) therethrough to permit the curable composition to cure within a desired period of time. This can be accomplished by providing, for example, a transparent, porous, open-weave, etc. pattern to the materials that are used to construct the sewing ring 202, skirt 260, stent frame 262, cover 280, etc.

Figure 3B:
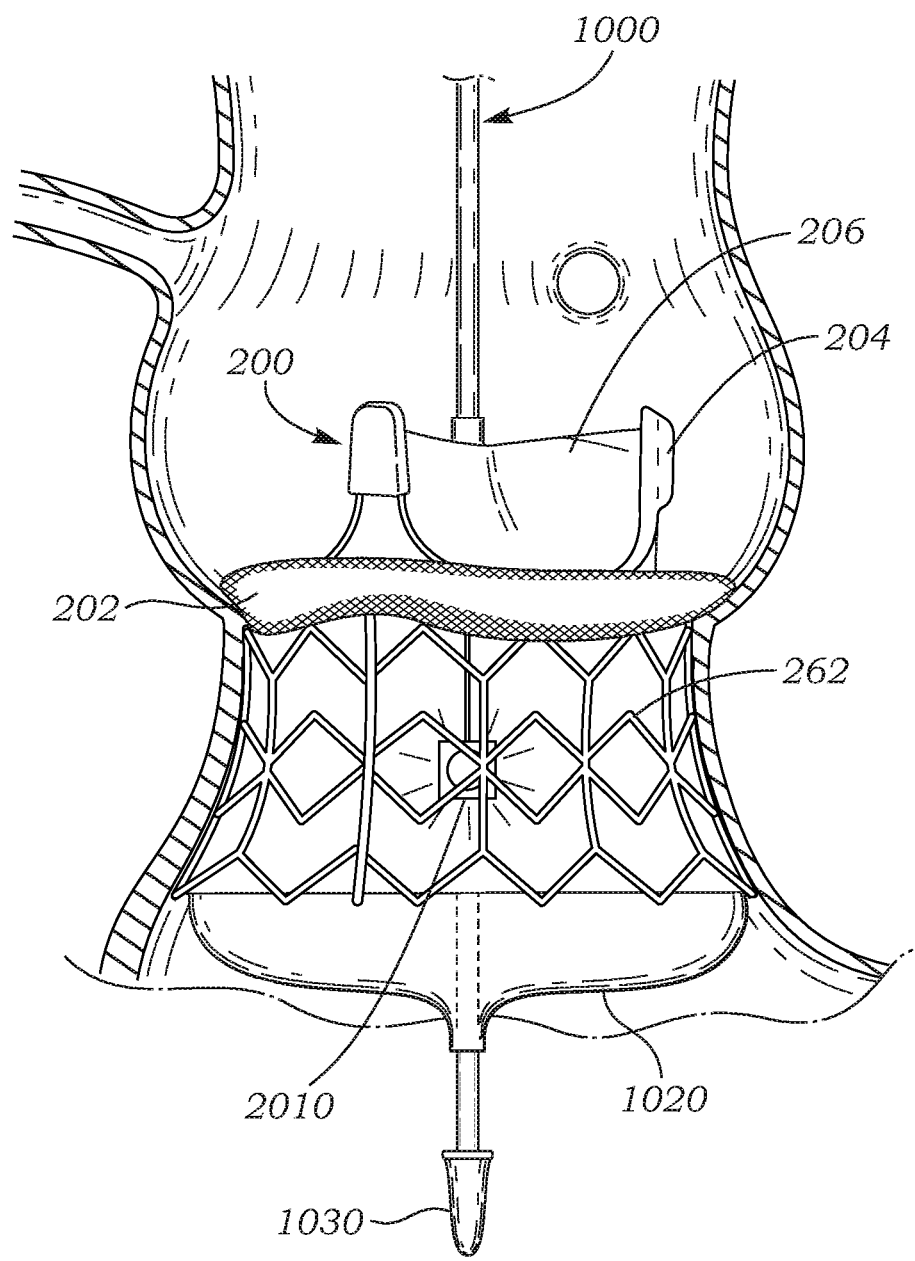

In one embodiment, as depicted in FIG. 3B, the energy source 2010 can be provided inside of the balloon 1020 of the balloon catheter 1000. The balloon can be constructed of a material that permits an effective amount of the curable energy to be transmitted therethrough, such as a transparent or other material depending on the type of energy that comprises the curable energy.

Figure 4A:
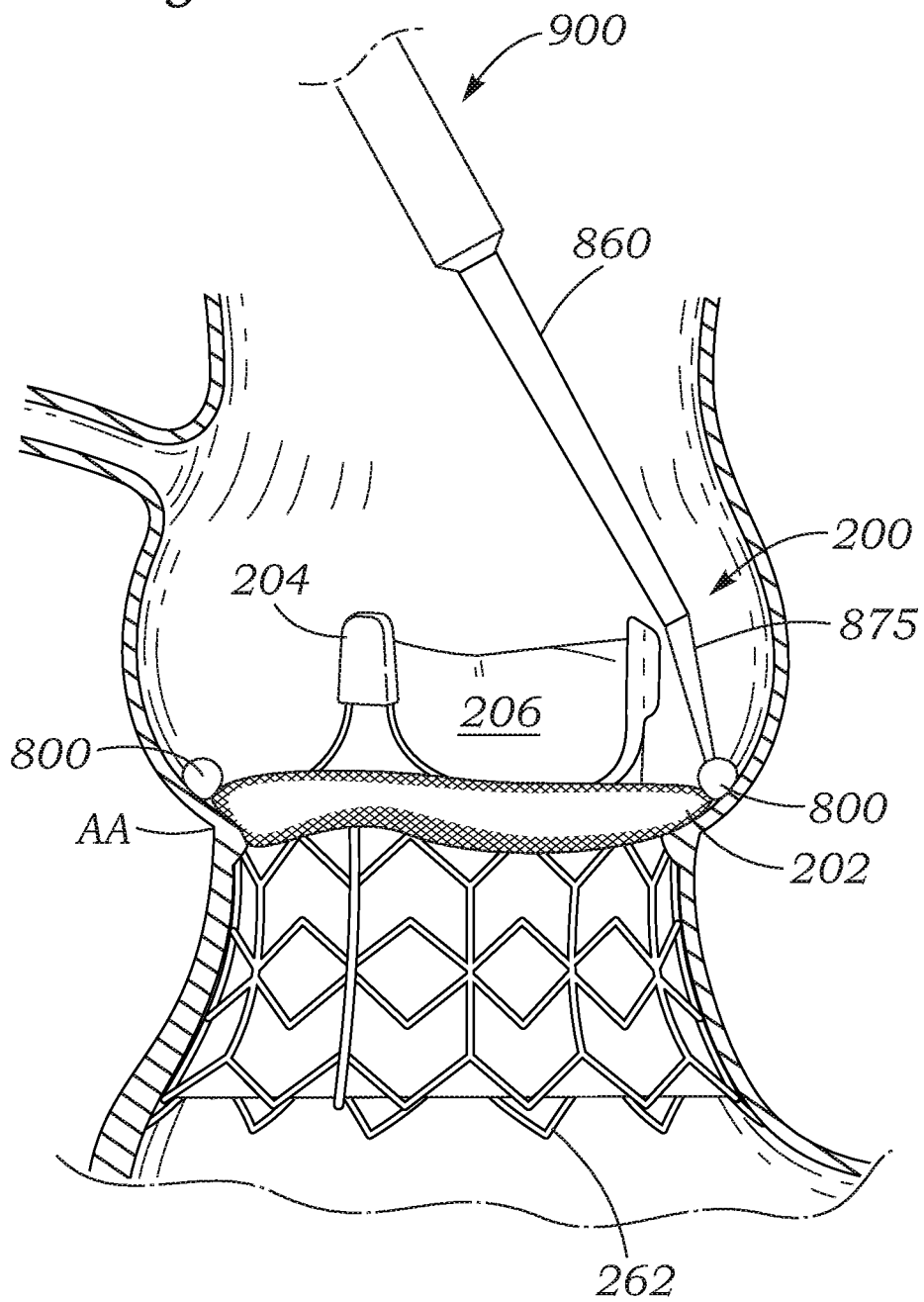
Figure 4B:
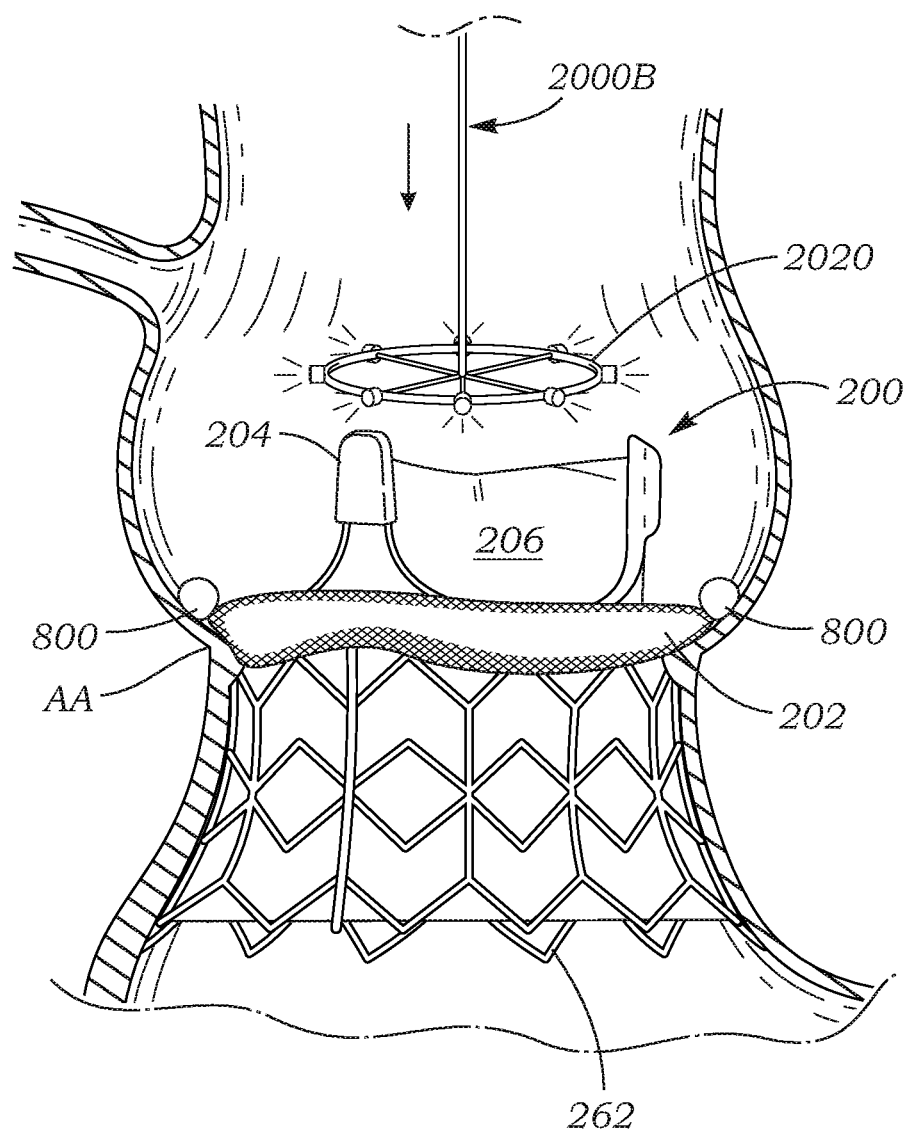

FIGS. 4A and 4B depict an exemplary embodiment of a method in which the curable composition or additional curable composition is applied after implantation of the aortic valve 200.

In FIG. 4A, an applicator 900 comprising the curable composition is used to deliver the curable composition to an interface between the aortic valve 200, specifically, the sewing ring 202 at the outflow side, and the aortic annulus AA. An angled end (e.g., 865, 870, 880, 885) of an extension tip 860 can be used to provide the needed maneuvering around the patient's anatomy and the implanted aortic valve 200 to position the curable composition 800 at the interface.

In FIG. 4B, the curable composition is cured using a probe 2000B. Because the curable composition 800 is applied around the substantially circularly shaped sewing ring 202, the energy source 2020 can be correspondingly shaped in a substantially circular configuration to deliver the curing energy to the curable composition 800.

Figure 5B:
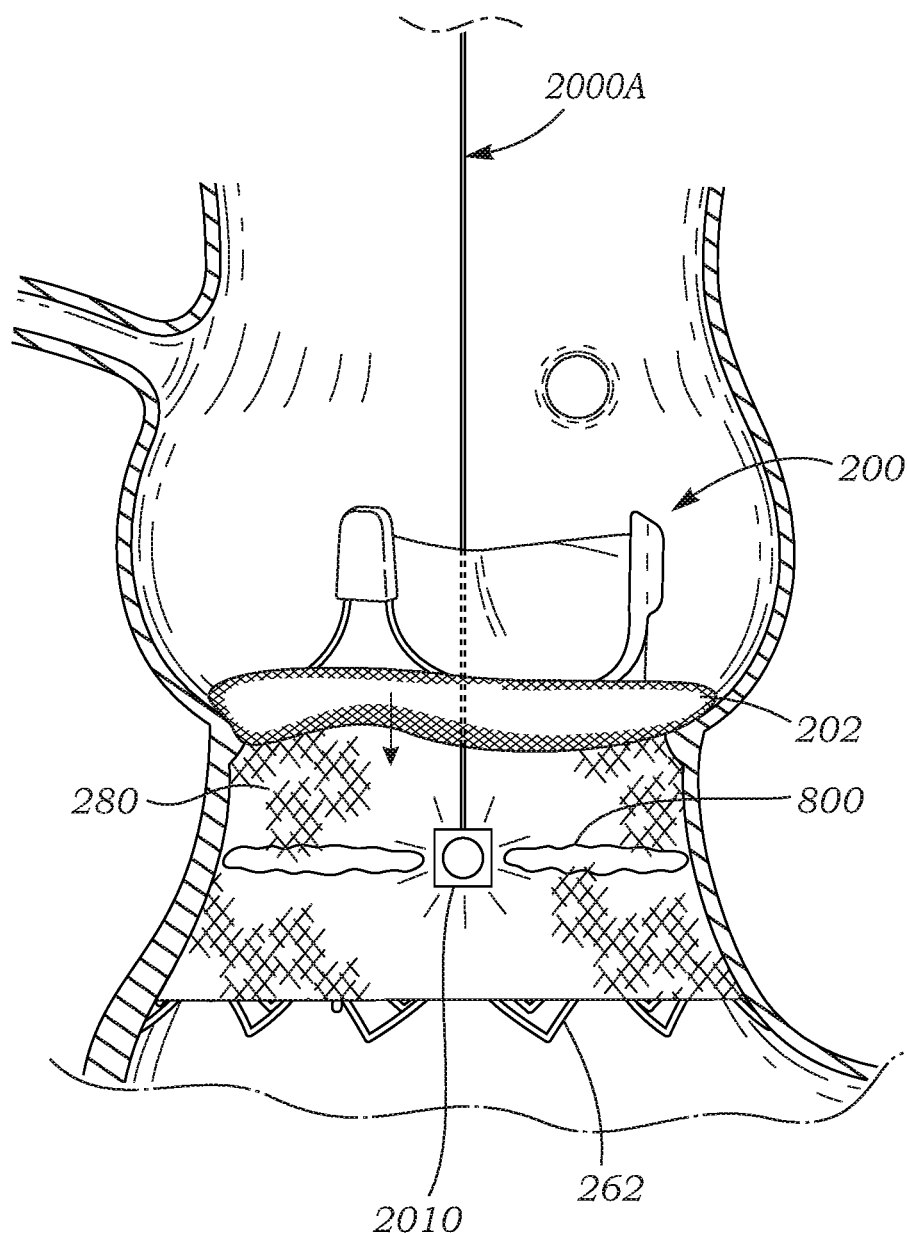

FIGS. 5A and 5B depict an exemplary embodiment of a method in which the curable composition is applied after implantation of the aortic valve 200.

In FIG. 5A, an applicator 900 comprising the curable composition is used to deliver the curable composition to an interface between the aortic valve 200, for example, the fabric 280 covering the stent frame 262 at the inflow side of the sewing ring 202, and the aortic wall. A hook-shaped-tip applicator 885 can be used to provide the needed maneuvering around the patient's anatomy and the implanted aortic valve 200 to insert and position the tip 885 between the fabric 280 and the aortic wall. The curable composition 800 can be delivered circumferentially around the aortic valve 200 or in desired areas where there can be a space between the aortic valve 200 and the aortic wall.

In FIG. 5B, the curable composition is cured using a probe (e.g., probe 2000A) with an energy source (e.g., energy source 2010). In the embodiment depicted in FIG. 5B, a smaller profile probe 2000A is required for insertion into the aortic valve 200 in order to deliver the curable energy to the curable composition 800 located between the skirt 260/fabric 280 and the aortic wall.

FIGS. 6A-6C depict the deployment of a prosthetic mitral valve within a mitral annulus MA.

Exemplary mitral valves and methods for implantation thereof are described in U.S. Pat. No. 6,966,925, issued on Nov. 22, 2005, the entire contents of which are incorporated herein by reference in its entirety.

FIG. 6A illustrates a plurality of implant sutures 628 that have been pre-threaded through the periphery of the mitral annulus MA and then through the sewing ring 620 of the prosthetic mitral valve 600. In an exemplary procedure/method, an array of implant sutures 628 is pre-threaded around the periphery of the mitral annulus MA and loose ends are removed from the surgical site to be threaded through the sewing ring 620 outside of the body. The mitral valve 600 is then parachuted down the array of sutures until it rests on the mitral annulus MA. A surgical handle 632 removably attaches to the holder 650 and facilitates manipulation and advancement of the holder/valve combination down the array of implant sutures 628.

The holder 650 removably attaches to the mitral valve 600, and this can be done using a plurality of lengths of flexible segments 636 which can be provided at the outflow end of the mitral valve 600. The holder 650 can further include an upstanding or shaft member 638 that extends along the flow axis of the valve and displaces the flexible segments 636 into the tent configuration shown in FIGS. 6A and 6B. The shaft member 638 can include a central bore or through-hole that permits the delivery of probes and other instruments, such as an applicator tip and/or an energy source, from the inflow end to the outflow end of the mitral valve 600. The flexible segments 636 extend radially inward from the outflow end of commissure posts 630 to the flow axis. Tension in the flexible segments 636 pulls the commissure posts 630 inward and also moves the first segments 636 upwards to form a steep angle, thus helping to prevent entanglement of any of the commissure posts with the array of implant sutures 628.

FIG. 6B shows the holder 650 and the mitral valve 600 assembled with the sewing ring 620 seated on the mitral annulus MA. The surgical handle 632 detaches from the holder 650, e.g., by unscrewing or, optionally, along with a handle interface of the holder by severing a flexible thread, as will be described below.

Once the handle 632 is removed to provide greater visibility, the surgeon can tie off the implant sutures 628 and sever them close to the sewing ring 620 to secure the mitral valve 600 in the annulus, as seen in FIG. 6C. The surgeon can then detach the holder 650 from the mitral valve 600 by severing each of the lengths of flexible material 636. Each length of the flexible material 636 is tied to the holder 650 at both ends, and severing it in the middle, at a cutting groove in the holder 650, permits the holder 650 with the lengths of flexible material attached, to be pulled free from the mitral valve 600.

The curable compositions can be utilized to help secure and/or seal the mitral valve 600 in the position as shown in FIG. 6C. This can be accomplished in a number of different methods, including any of the methods described here or elsewhere in this disclosure. In one embodiment, the curable composition can be applied directly onto the mitral annulus MA and/or other tissue prior to the introduction of the mitral valve 600 and/or after the introduction of the mitral valve 600. For example, an applicator (e.g., applicator 900 depicted in 4A, 5A, 8A, 9A, 10, etc.) can be used to extrude the curable composition through an extrusion tip or catheter (e.g., extrusion tip 860, 865, 870, 880, 885, etc.).

Optionally, the curable composition can instead or also be applied to mitral valve 600 at the peripheral surface of the sewing ring 620 using an applicator (e.g., applicator 150 or applicator 900 depicted in FIGS. 4A, 5A, 8A, 9A, 10, etc.) and/or an extrusion tip/catheter (e.g., extrusion tip 860, 865, 870, 880, 885, etc.). This can be done just prior to the introduction of the mitral valve 600 into the patient's body and/or after introduction of the mitral valve 600 into the patient's body.

Figure 7:
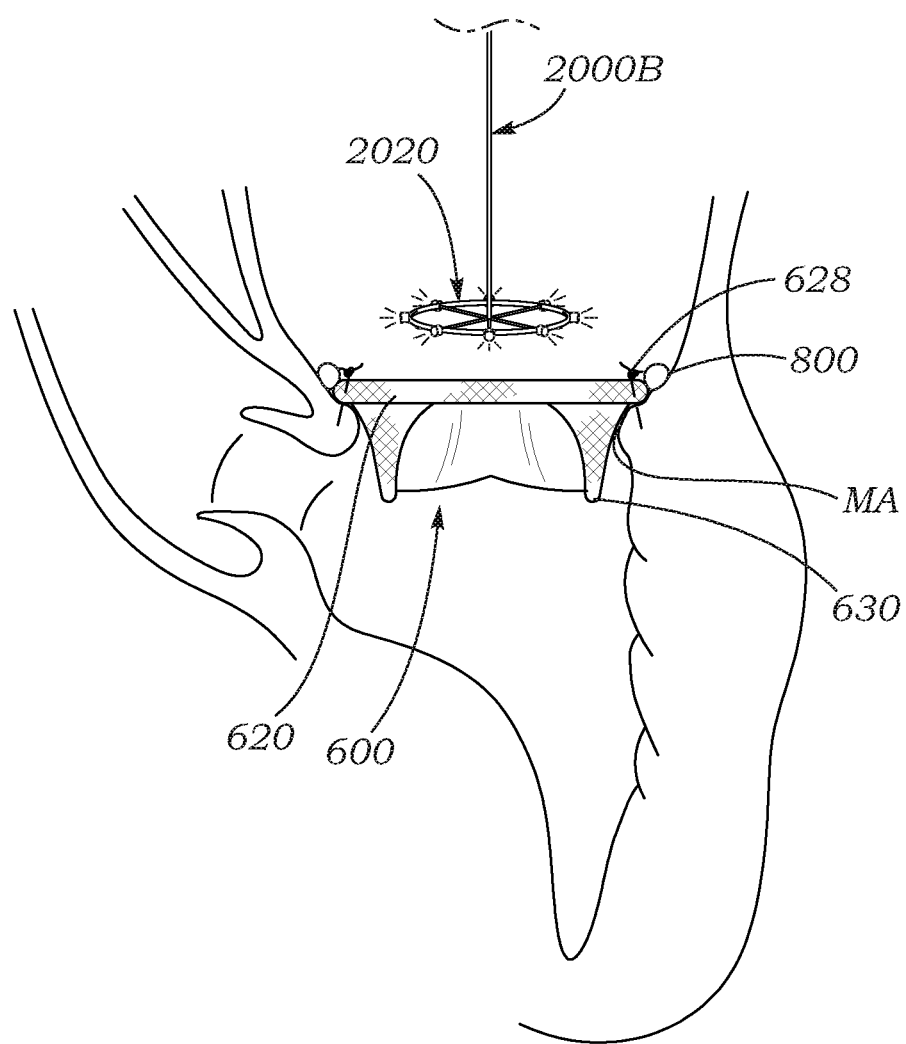
FIG. 7 depicts the energy source advancing toward the sewing ring to be positioned around or within the sewing ring to cure the curable composition.

An energy source that effectively cures the curable composition can be applied after implantation as depicted, for example, in FIG. 7, including in embodiments in which the curable composition is applied directly on to the mitral annulus MA and/or on the mitral valve 600.

FIG. 7 depicts a probe 2000B that comprises an energy source 2020 effective to cure the curable composition. In one embodiment, the energy source 2020 can be electromagnetic radiation or thermal energy, which is provided at the end of an elongated shaft. The elongated shaft can be rigid, semi-rigid, pliable, flexible, etc. at one or more location along its length so as to enable it to be shaped in a manner that will allow it to be positioned near the location in which the curable composition is applied. In FIG. 7, the curable composition/adhesive 800 is provided between the sewing ring 620 and the mitral annulus MA. The energy source 2020 can be advanced proximate or inside the mitral valve 600 and can be positioned adjacent the sewing ring 620 to apply curing energy to the curable composition 800. The sewing ring 620 can be constructed of a material that permits the transmission of an effective amount of the energy (e.g., electromagnetic radiation, UV light, thermal energy, etc.) therethrough to permit the curable composition to cure within a desired period of time. This can be accomplished by providing, for example, a transparent, porous, open-weave pattern, etc. to the materials that are used to construct the sewing ring 620 and/or other portions of the valve 600. Moreover, due to the orientation of the mitral valve in which the inflow end is proximal to the surgical approach, energy source 2020 can be configured in a circular shape, e.g., as depicted in FIG. 7.

Figure 8A:
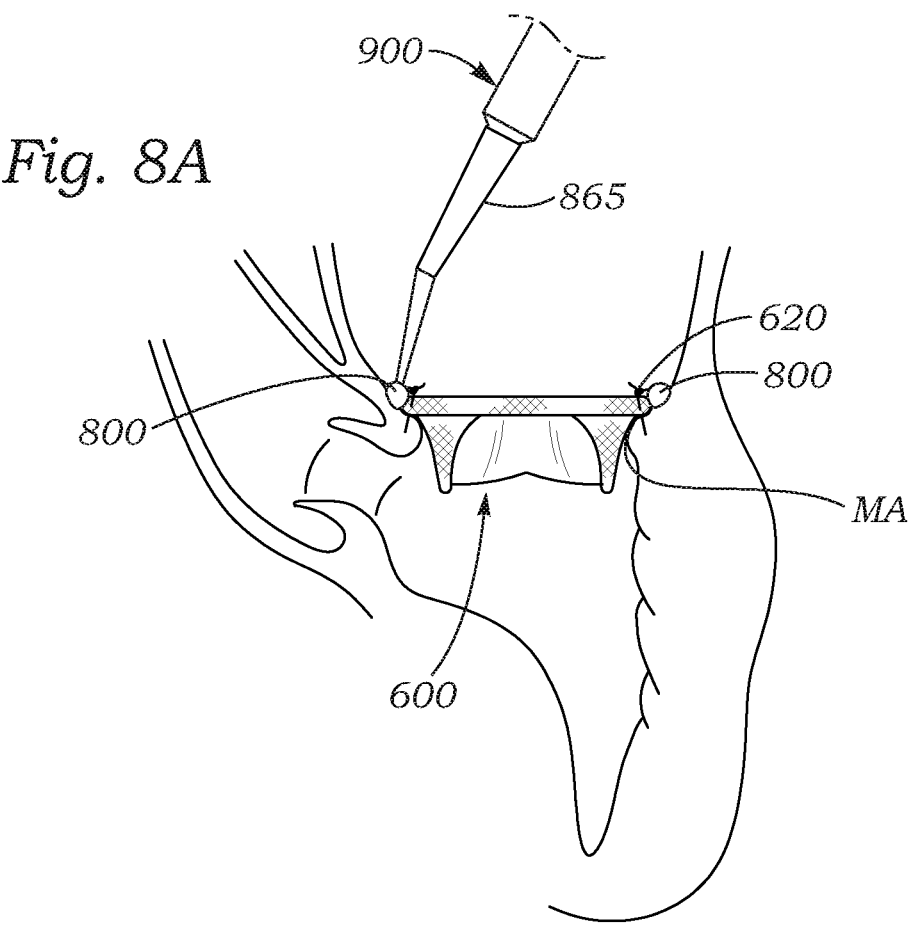
Figure 8B:
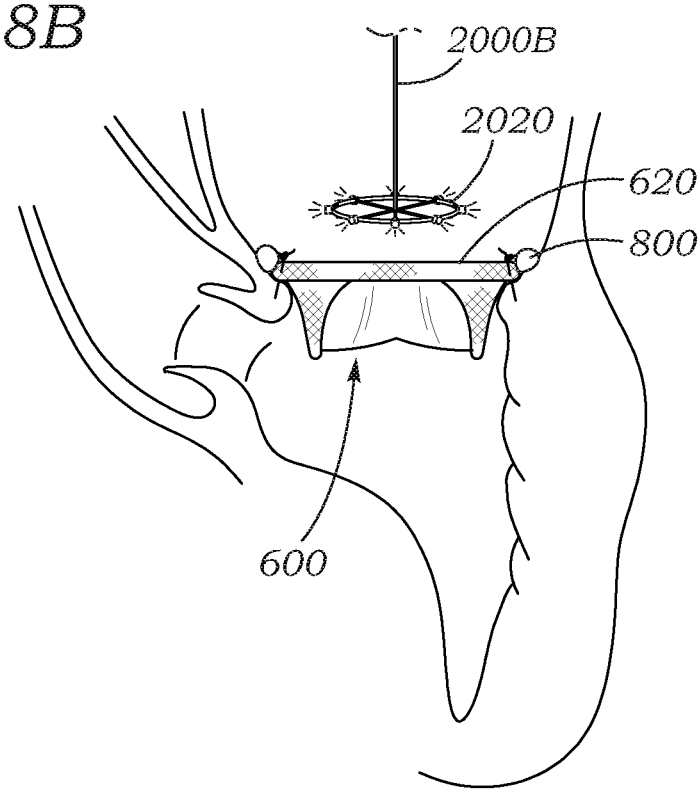

FIGS. 8A and 8B depict one exemplary embodiment of a method in which the curable composition or additional curable composition is applied after implantation of the mitral valve 600.

In FIG. 8A, an applicator 900 comprising the curable composition is used to deliver the curable composition to an interface between the mitral valve 600, optionally, the sewing ring 620 at the inflow side, and the mitral annulus MA. An extrusion tip (e.g., extrusion tip 860, 865, 870, 880, 885, etc.) can be used to apply the curable composition. The extrusion tip can include an angled portion to provide better maneuvering around the patient's anatomy and the implanted mitral valve 600 to position the curable composition 800 at the interface.

In FIG. 8B, the curable composition is cured using a probe 2000B including an energy source 2020. As the curable composition 800 is applied around the substantially circularly shaped sewing ring 620, the energy source 2020 can be correspondingly shaped in a substantially circular configuration to deliver the curing energy to the curable composition 800.

Figure 9B:
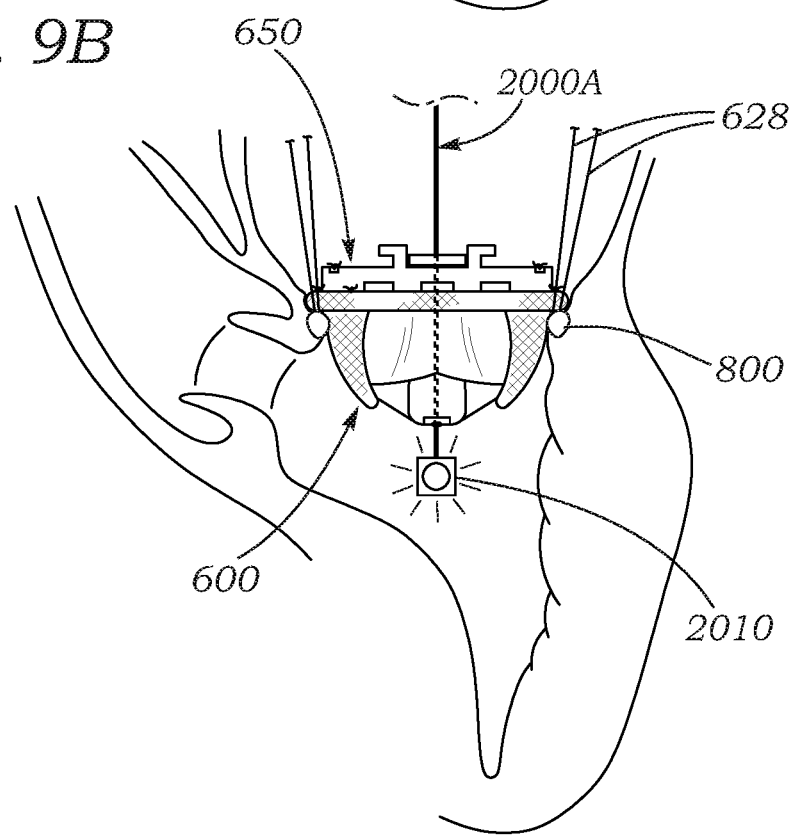

FIGS. 9A and 9B depict another embodiment of a method in which the curable composition is applied after implantation of the mitral valve 600.

In FIG. 9A, an applicator (e.g., applicator 900) comprising the curable composition is used to deliver the curable composition to an interface between the mitral valve 600 at the inflow side of the sewing ring 620, and the mitral annulus. A hook-shaped-tip applicator 885 can be used to provide the needed maneuvering around the patient's anatomy and the implanted aortic valve 200 to insert and position the tip 885 between the mitral valve 600 and the mitral annulus. The curable composition 800 can be delivered circumferentially around the mitral valve 600 or in desired areas where there can be a space between the mitral valve 600 and the mitral annulus.

In FIG. 9B, the curable composition is cured using a probe (e.g., probe 2000A and an energy source (e.g., energy source 2010). In the embodiment depicted in FIG. 9B, a smaller profile probe 2000A is used for insertion into and/or through the mitral valve 600 in order to deliver the curable energy to the curable composition 800 located between mitral valve 600 and the mitral annulus.

The curable composition 800 can be delivered to one or both of the commissure posts 630 and/or at the interface between the sewing ring 620 and the mitral annulus. To that end, the holder 650 can remain secured to the mitral valve 600 as it comprises a central bore through which the applicator/extrusion tip and the energy source can be delivered to the outflow area of the mitral valve 600. The applicator/extrusion tip is preferably resiliently pliable or flexible to permit it to be threaded through the central bore hole of the holder 650. Moreover, implant sutures 628 can remain to bias the commissure posts 630 radially inwardly so as to facilitate access by the applicator/extrusion tip to the outflow side of the sewing ring 620.

The curable compositions suitable for use in connection with the implantable medical devices described herein can comprise a crosslinking pre-polymer and an initiator. Exemplary curable compositions that can be used in connection with the implantable medical devices disclosed herein are described in U.S. Patent Application Publication No. 2014/0348896, published Nov. 27, 2014, the entire contents of which are incorporated herein by reference. In a preferred embodiment, the pre-polymer comprises one or more of the following characteristics: (1) the pre-polymer has a sufficient viscosity such that it withstands the hemodynamic forces and resists being washed off the site of application; (2) the pre-polymer is not reactive with or does not crosslink in the presence of bodily fluids and, in particular, blood; (3) the pre-polymer is hydrophobic; (4) the pre-polymer is capable of adhering to wet tissue; (5) the pre-polymer is biocompatible; and (6) the pre-polymer is biodegradable.

In one embodiment, the pre-polymer is activated by introduction of one or more functional groups (i.e., incorporated on the pre-polymer backbone) that can be reacted to form crosslinks between polymer chains. In one embodiment, the functional groups can be selected from the group consisting of: substituted vinyl groups, unsubstituted vinyl groups, substituted acrylate groups, unsubstituted acrylate groups, vinyl esters, vinyl carbamates, vinyl ketones, vinyl amides, vinyl carbonates, vinyl ether groups or vinyl groups in the form of allyl. In one embodiment, the polymer chain is polyester formed from a substituted or unsubstituted polyol, such as a triol, and a substituted or unsubstituted diacid. The triol can be glycerol. The functional groups can also form crosslinks with the tissue. The degree of activation can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, or 1.5. The degree of activation can be provided within a range of between and including any two of the foregoing values.

The degree of activation can be selected based on whether the curable composition is a sealant or an adhesive. Generally, the degree of activation for a sealant is expected to be lower than the degree of activation for an adhesive.

In one embodiment, the curable composition comprises or consists of a sealant and the pre-polymer has a degree of activation that is about 0.5 or less, about 0.4 or less, about 0.3 or less, about 0.2 or less, about 0.1 or less, about 0.09 or less, about 0.08 or less, about 0.07 or less, about 0.06 or less, about 0.05 or less, about 0.04 or less, about 0.03 or less, about 0.02 or less, about 0.01 or less, about 0.009 or less, about 0.008 or less, about 0.007 or less, about 0.006 or less, about 0.005 or less, about 0.004 or less, about 0.003 or less, about 0.002 or less, or about 0.001 or less.

In another embodiment, the curable composition comprises or consists of an adhesive and the pre-polymer as a degree of activation that is about 0.5 or greater, 0.6 or greater, 0.7 or greater, 0.8 or greater, 0.9 or greater, 0.1 or greater, 0.2 or greater, 0.3 or greater, 0.4 or greater, 0.5 or greater, 0.6 or greater, 0.7 or greater, 0.8 or greater, 0.9 or greater, 1.0 or greater, 1.1 or greater, 1.2 or greater, 1.3 or greater, 1.4 or greater, or 1.5 or greater.

The viscosity of the pre-polymer of the curable composition depends in part upon the molecular weight of the pre-polymer, with higher molecular weight pre-polymers giving rise to more viscous compositions. In one embodiment, the pre-polymer can also have a molecular weight of about 1,000 Daltons or more, about 2,000 Daltons or more, about 3,000 Daltons or more, about 4,000 Daltons or more, about 5,000 Daltons or more, about 6,000 Daltons or more, about 7,000 Daltons or more, about 8,000 Daltons or more, about 9,000 Daltons or more, about 10,000 Daltons or more, about 11,000 Daltons or more, about 12,000 Daltons or more, about 13,000 Daltons or more, about 14,000 Daltons or more, about 15,000 Daltons or more, about 16,000 Daltons or more, about 17,000 Daltons or more, about 18,000 Daltons or more, about 19,000 Daltons or more, about 20,000 Daltons or more, about 21,000 Daltons or more, about 22,000 Daltons or more, about 23,000 Daltons or more, about 24,000 Daltons or more, about 25,000 Daltons or more, about 26,000 Daltons or more, about 27,000 Daltons or more, about 28,000 Daltons or more, about 29,000 Daltons or more, about 30,000 Daltons or more, about 35,000 Daltons or more, about 40,000 Daltons or more, about 45,000 Daltons or more, about 50,000 Daltons or more, about 55,000 Daltons or more, about 60,000 Daltons or more, about 65,000 Daltons or more, about 70,000 Daltons or more, about 75,000 Daltons or more, about 80,000 Daltons or more, about 85,000 Daltons or more, about 90,000 Daltons or more, about 95,000 Daltons or more, or about 100,000 Daltons or more. The molecular weight of the pre-polymer can be provided within a range between and including any two of the foregoing values. For example, the molecular weight range can be from about 3,000 Daltons to about 10,000 Daltons.

In one embodiment, the curable composition comprises or consists of a sealant and the pre-polymer can have any one of the above-recited molecular weights. For example, the pre-polymer can have a molecular weight of about 11,000 Daltons or greater.

In another embodiment, the curable composition comprises or consists of an adhesive and the pre-polymer can have any of above-recited molecular weights. For example, the pre-polymer can have a molecular weight of about 1,000 Daltons to about 10,000 Daltons.

The desired viscosity of the pre-polymer can be tuned based, in part, on the molecular weight of the pre-polymer. In one embodiment, the desired viscosity can be selected to provide a pre-polymer that to remain in place at the site of application without being washed away by bodily fluids. The viscosity of the pre-polymer can be about 0.5 Pa·s or more, 1 Pa·s or more, 2 Pa·s or more, 3 Pa·s or more, 4 Pa·s or more, 5 Pa·s or more, 6 Pa·s or more, 7 Pa·s or more, 8 Pa·s or more, 9 Pa·s or more, 10 Pa·s or more, 11 Pa·s or more, 12 Pa·s or more, 13 Pa·s or more, 14 Pa·s or more, 15 Pa·s or more, 16 Pa·s or more, 17 Pa·s or more, 18 Pa·s or more, 19 Pa·s or more, 20 Pa·s or more, 21 Pa·s or more, 22 Pa·s or more, 23 Pa·s or more, 24 Pa·s or more, 25 Pa·s or more, 26 Pa·s or more, 27 Pa·s or more, 28 Pa·s or more, 29 Pa·s or more, 30 Pa·s or more, 31 Pa·s or more, 32 Pa·s or more, 33 Pa·s or more, 34 Pa·s or more, 35 Pa·s or more, 36 Pa·s or more, 37 Pa·s or more, 38 Pa·s or more, 39 Pa·s or more, 40 Pa·s or more, 41 Pa·s or more, 42 Pa·s or more, 43 Pa·s or more, 44 Pa·s or more, 45 Pa·s or more, 46 Pa·s or more, 47 Pa·s or more, 48 Pa·s or more, 49 Pa·s or more, 50 Pa·s or more, 51 Pa·s or more, 52 Pa·s or more, 53 Pa·s or more, 54 Pa·s or more, 55 Pa·s or more, 56 Pa·s or more, 57 Pa·s or more, 58 Pa·s or more, 59 Pa·s or more, 60 Pa·s or more, 61 Pa·s or more, 62 Pa·s or more, 63 Pa·s or more, 64 Pa·s or more, 65 Pa·s or more, 66 Pa·s or more, 67 Pa·s or more, 68 Pa·s or more, 69 Pa·s or more, 70 Pa·s or more, 71 Pa·s or more, 72 Pa·s or more, 73 Pa·s or more, 74 Pa·s or more, 75 Pa·s or more, 76 Pa·s or more, 77 Pa·s or more, 78 Pa·s or more, 79 Pa·s or more, 80 Pa·s or more, 81 Pa·s or more, 82 Pa·s or more, 83 Pa·s or more, 84 Pa·s or more, 85 Pa·s or more, 86 Pa·s or more, 87 Pa·s or more, 88 Pa·s or more, 89 Pa·s or more, 90 Pa·s or more, 91 Pa·s or more, 92 Pa·s or more, 93 Pa·s or more, 94 Pa·s or more, 95 Pa·s or more, 96 Pa·s or more, 97 Pa·s or more, 98 Pa·s or more, 99 Pa·s or more, or 100 Pa·s or more. The viscosity can be provided within a range between and including any two of the foregoing values. For example, the range for viscosity can be from about 0.5 Pa·s to about 50 Pa·s.

The pre-polymer is optionally formed by the reaction of a polyol and a polyacid. The polyol can be one or a combination of compounds comprising two or more hydroxyl groups, including diols, alkane diols, triols, glycerol, trimethylolpropane, triethanolamine, tetraols, erythritol, pentaerythritol, sorbitol, unsaturated diols, tetradeca-2,12-diene-1,1,14-diol, macromonomer diols, polyethylene oxide, or N-methyldiethanolamine. The polyacid can be a diacid or higher order acid and include, for example, glutaric acid, adipic acid, pimelic acid, suberic acid, and azelaic acid. Exemplary long chain acids can include diacids having 5 or more, 10 or more, 15 or more, 20 or more, or 25 or more carbon atoms.

In one embodiment, the pre-polymer is a poly(glycerol sebacate) (PGS) pre-polymer prepared through the polycondensation of equimolar amounts of glycerol and sebacic acid.

The curable composition can comprise an initiator. In one embodiment the initiator is a photoinitiator. In one embodiment, the photoinitiator can be selected from the group consisting of 2-dimethoxy-2-phenyl-acetophenone, 2-hydroxy-1-[4-(hydroxyethoxy)phenyl]-2-methyl-1-propanone (IRGACURE® 2959), 1-hydroxycyclohexyl-1-phenyl ketone (IRGACURE® 184), 2-hydroxy-2-methyl-1-phenyl-1-propanone (DAROCUR® 1173), 2-benzyl-2-(dimethylamino)-1-[4-morpholinyl)phenyl]-1-butanone (Irgacure 369), methylbenzoylformate (DAROCUR® MBF), oxyphenyl-acetic acid-2-[2-oxo-2-phenyl-acetoxy-ethoxy]-ethyl ester (IRGACURE® 754), 2-methyl-1-[4-(methylthio)phenyl]-2-(4-morpholinyl)-1-propanone (IRGACURE® 907), diphenyl(2,4,6-trimethylbenzoyl)-phosphine oxide (DAROCUR® TPO), phosphine oxide, phenyl bis(2,4,6-trimethyl benzoyl) (IRGACURE® 819), and combinations thereof. In one embodiment, the preferred photoinitiator is IRGACURE® 2959.

The pre-polymer can be crosslinked by photopolymerization by exposure to electromagnetic radiation, such as visible or UV light. The exposure time can be varied in order to achieve the desired amount of crosslinking. In one embodiment, the irradiation time is about 1 second, 5 seconds, 10 seconds, 15 seconds, 20 seconds, 30 seconds, 45 seconds, one minute, 90 seconds, or two minutes or greater. The irradiation time is provided can be in a range between and including any two values. The intensity of the light can be varied as needed to achieve sufficient crosslinking. In one embodiment, the intensity is less than about 0.45 W/cm$^2$.

The crosslink density in the cured polymer can be tuned by varying the degree of activation, e.g., acrylation, of the pre-polymer or by varying the curing conditions, such as cure time and the intensity of the energy that is applied to cure the pre-polymer. A greater adhesive strength is believed to be achieved by higher levels of crosslinking.

Where the resulting cross-linked polymer comprises a sealant, it can have a crosslinking density of about 10% or less, about 9% or less, about 8% or less, about 7% or less, about 6% or less, about 5% or less, about 4% or less, about 3% or less, about 2% or less, about 1% or less, about 0.5% or less, about 0.1% or less, about 0.05% or less, about 0.01% or less, about 0.005% or less, or about 0.001% or less. The resulting cross-linked polymer can have a crosslinking density within a range of between and including any two of the foregoing values.

Where the resulting cross-linked polymer comprises an adhesive, it can have a crosslinking density of about 1% or more, about 2% or more, about 3% or more, about 4% or more, about 5% or more, about 6% or more, about 7% or more, about 8% or more, about 9% or more, about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, or about 80% or more. The resulting cross-linked polymer can have a crosslinking density within a range of between and including any two of the foregoing values. The greater the crosslink density, the greater the polymer cohesion and adhesive strength.

The resulting cross-linked polymer can be configured to adhere to wet tissue. In one embodiment in which the cross-linked polymer is an adhesive, the cross-linked polymer has an adhesion strength that is sufficient to secure the implantable medical device to the anatomical feature or tissue, preferably without the need for additional securing mechanisms such as sutures or staples. Depending on the forces that can act upon the cross-linked polymer at the site of application, such as hemodynamic forces, the adhesive strength can be about 0.1 N/cm$^2$ or greater, about 0.2 N/cm$^2$ or greater, about 0.3 N/cm$^2$ or greater, about 0.4 N/cm$^2$ or greater, about 0.5 N/cm$^2$ or greater, about 0.6 N/cm$^2$ or greater, about 0.7 N/cm$^2$ or greater, about 0.8 N/cm$^2$ or greater, about 0.9 N/cm$^2$ or greater, about 1.0 N/cm$^2$ or greater, about 1.1 N/cm$^2$ or greater, about 1.2 N/cm$^2$ or greater, about 1.3 N/cm$^2$ or greater, about 1.4 N/cm$^2$ or greater, about 1.5 N/cm$^2$ or greater, about 1.6 N/cm$^2$ or greater, about 1.7 N/cm$^2$ or greater, about 1.8 N/cm$^2$ or greater, about 1.9 N/cm$^2$ or greater, about 2.0 N/cm$^2$ or greater, about 2.1 N/cm$^2$ or greater, about 2.2 N/cm$^2$ or greater, about 2.3 N/cm$^2$ or greater, about 2.4 N/cm$^2$ or greater, about 2.5 N/cm$^2$ or greater, about 2.6 N/cm$^2$ or greater, about 2.7 N/cm$^2$ or greater, about 2.8 N/cm$^2$ or greater, about 2.9 N/cm$^2$ or greater, about 3.0 N/cm$^2$ or greater, about 3.5 N/cm$^2$ or greater, about 4.0 N/cm$^2$ or greater, about 4.5 N/cm$^2$ or greater, about 5.0 N/cm$^2$ or greater, about 5.5 N/cm$^2$ or greater, about 6.0 N/cm$^2$ or greater, about 6.5 N/cm$^2$ or greater, about 7.0 N/cm$^2$ or greater, about 7.5 N/cm² or greater, about 8.0 N/cm² or greater, about 8.5 N/cm² or greater, about 9.0 N/cm² or greater, about 9.5 N/cm² or greater, or about 10.0 N/cm² or greater. The adhesion strength can be provided in a range between and including any two of the foregoing values.

Where the cross-linked polymer comprises a sealant, the cross-linked polymer can have an adhesion strength that is sufficient to permit the cross-linked polymer to remain at the site of application. In some embodiments, the implantable medical device can be adhered to the anatomical feature without the need for sutures or additional means for securing the device. The sealant can have the adhesive strength to secure the implantable medical device to the anatomical feature. In some embodiments, the sealant need only be strong enough to resist becoming dislodged from the site of application by the hemodynamic forces that can act upon it. In some embodiments, sutures or additional means for securing the device can optionally be used with the sealant. In one embodiment, the adhesive strength of the sealant is about 0.1 N/cm² or less, about 0.09 N/cm² or less, about 0.08 N/cm² or less, about 0.07 N/cm² or less, about 0.06 N/cm² or less, about 0.05 N/cm² or less, about 0.04 N/cm² or less, about 0.03 N/cm² or less, about 0.02 N/cm² or less, about 0.01 N/cm² or less, about 0.009 N/cm² or less, about 0.008 N/cm² or less, about 0.007 N/cm² or less, about 0.006 N/cm² or less, about 0.005 N/cm² or less, about 0.004 N/cm² or less, about 0.003 N/cm² or less, about 0.002 N/cm² or less, or about 0.001 N/cm² or less. The wet adhesion can be provided in a range between and including any two of the foregoing values.

FIGS. 12A-12B depict one embodiment of a combined implantable heart valve delivery device 3000 that can be provided in a retracted state (FIG. 12A) for delivering a compressed implant device 3500 (e.g., a heart valve, etc.) to a desired anatomical location in a patient and in an expanded state (FIG. 12B) for implantation and sealing of the implant device 3500 at the desired anatomical location. The implant device 3500 can be self-expanding, balloon-expandable, and/or mechanically expandable. The delivery device 3000 can comprise a handle 3100, an outer sheath 3200, a delivery catheter 3300 movably disposed within the outer sheath 3200, an expandable implant device 3500 (e.g., expandable heart valve) coupled to the delivery catheter 3300, an inflatable balloon 3400 disposed at a distal end of the delivery catheter 3300, and/or other features/components/variations.

FIG. 12A depicts the delivery device 3000 in a retracted position ready for delivering the compressed implant device 3500 (e.g., compressed heart valve) close to or at a desired anatomical location for implantation. As can be seen, the outer sheath 3200 houses the delivery catheter 3300, the implant device 3500 and the inflatable balloon 3400. Once the delivery device 3000 is appropriately positioned at or near the desired anatomical location for implantation, the delivery catheter 3300 can be advanced distally of the handle 3100 by advancing the delivery catheter 3300 through the inlet port 3120.

FIG. 12B depicts the delivery device 3000 in a fully deployed state for implanting the implant device 3500 at the desired anatomical location. As is shown, the delivery catheter 3300 is extended distally of the handle 3100 and the balloon 3400 is provided in an inflated configuration.

An energy source, such as a fiber optic 3310, is movably provided within a lumen of the delivery catheter 3300 and can be advanced distally and into the balloon 3400 to emit a curing energy, such as UV light, by a sliding actuator 3110 on the handle 3100. The UV light can be used to cure the curable composition after the implant device 3500 has been implanted at the desired anatomical location and the curable composition has been provided between the implant device 3500 and the anatomical location.

In one embodiment, the UV light is typically emitted from the fiber optic 3310 at an angle θ relative to a central axis, as shown in FIG. 12B. An inflatable balloon 3400 can be provided to direct the emitted UV light to a desired location. The inflatable balloon 3400 can be configured to have a particular geometric configuration in which portions of the inflatable balloon 3400 are selected to reflect the emitted UV light and portions of the inflatable balloon 3400 are selected to transmit the emitted UV light.

Thus, the angle θ at which the UV light is emitted from the fiber optic 3310, the shape of the balloon 3400 and the portions of the balloon 3400 selected to reflect and transmit light will determine the location to which the UV light emitted by the fiber optic 3310 is directed.

In one embodiment, the angle θ at which the UV light is emitted from the fiber optic 3310 relative to a central axis can be about 20° or more, about 21° or more, 22° or more, about 23° or more, about 24° or more, about 25° or more, about 26° or more, about 27° or more, about 28° or more, about 29° or more, about 30° or more, about 31° or more, about 32° or more, about 33° or more, about 34° or more, about 35° or more, about 36° or more, about 37° or more, about 38° or more, about 39° or more, about 40° or more, about 41° or more, about 42° or more, about 43° or more, about 44° or more, about 45° or more, about 46° or more, about 47° or more, about 48° or more, about 49° or more, about 50° or more, about 51° or more, about 52° or more, about 53° or more, about 54° or more, about 55° or more, about 56° or more, about 57° or more, about 58° or more, about 59° or more, or about 60° or more. In another embodiment, the angle θ can be provided in a range between and including any two of the foregoing values.

In the embodiment depicted in FIG. 12B, the angle θ at which the UV light is emitted from the fiber optic 3310 is from about 22° to about 45° relative to the central axis. Considering the angle θ at which the UV light is emitted, the balloon 3400 has a frusto-conical shape having a narrow distal end 3410, a wide proximal end 3430 and an angled side wall 3420 between the narrow distal end 3410 and the wide proximal end 3430. The narrow distal end 3410 and the angled side wall 3420 is provided with a reflective surface and the wide proximal end 3430 is provided with a light transmissive surface. In this embodiment, the narrow distal end 3410 and the angled side wall 3420 reflects the emitted UV light back down through the wide proximal end 3430 and onto the stented implant device 3500.

In the embodiment depicted in FIGS. 12A-12B, a single inlet port 3120 is provided and the delivery catheter 3300 comprises a plurality of lumens to advance and deliver a guide wire to guide the delivery catheter 3300 to its intended location, to deliver an inflating fluid to the balloon 3400 and to guide the fiber optic 3310 along the length of the delivery catheter 3300 and into the balloon 3400.

Figure 13A:
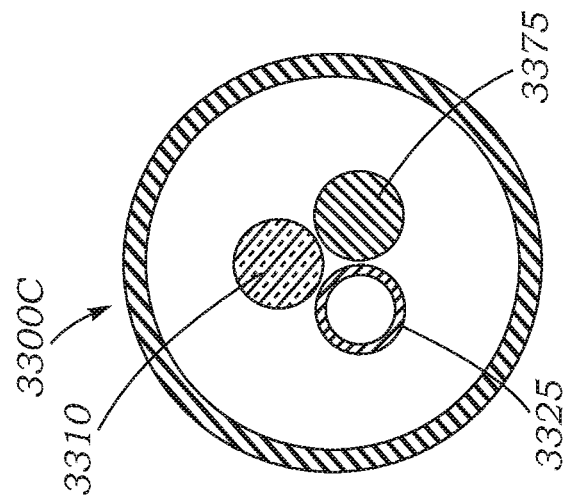
FIGS. 13A-13C are cross-sectional views of various different exemplary embodiments of the inner catheter housing the flush port, the guide-wire and the fiber-optic.
Figure 13B:
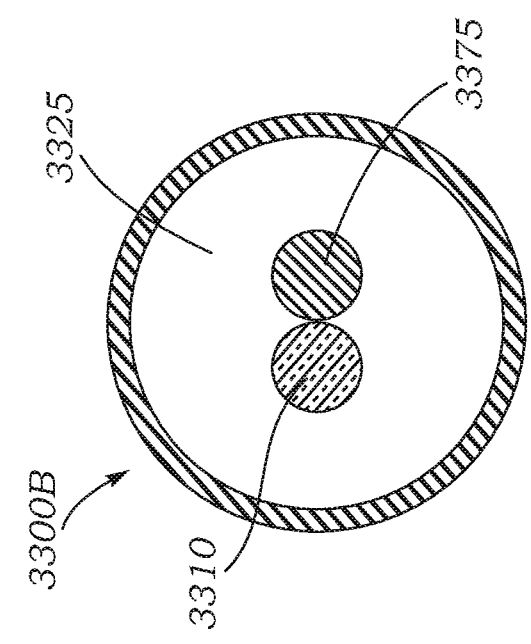
Figure 13C:
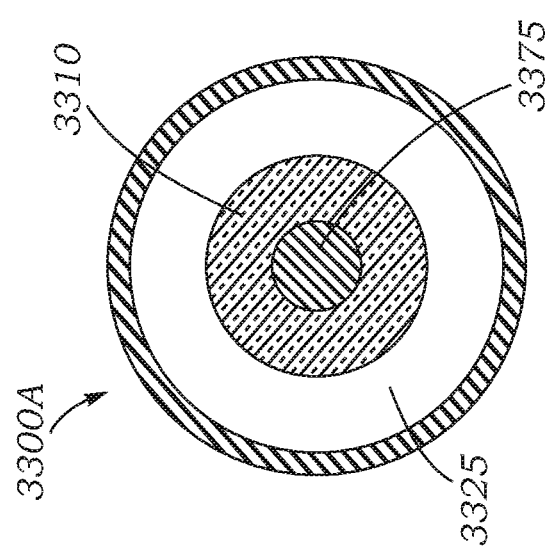

The plurality of lumens in the delivery catheter 3300 can be arranged in any number of ways. FIGS. 13A-13C depict cross-sectional views of various different embodiments of the inner catheter housing the flush port, the guide-wire and the fiber-optic. In one optional embodiment, as depicted in FIG. 13A, the delivery catheter 3300A can include separate and discrete flush 3325, fiber optic 3310 and guide wire lumens 3375 in a concentric arrangement, with the flush lumen 3325 preferably having the greatest volume and the fiber optic lumen 3310 being provided between the guide wire lumen 3375 and the flush lumen 3325. In another optional embodiment, as depicted in FIG. 13B, the delivery catheter 3300B can include separate and discrete flush, fiber optic and guide wire lumens in which the flush lumen 3325 surrounds both the fiber optic lumen 3310 and guide wire lumen 3375, which are arranged side-by-side. In a further optional embodiment, depicted in FIG. 13C, the delivery catheter 3300C can include the flush lumen 3325, the fiber optic lumen 3310 and the guide wire lumen 3375 as separate and discrete lumens arranged side-by-side.

FIGS. 14A-14B depict one embodiment of a combined implantable heart valve delivery device 4000 that can be provided in a retracted state (FIG. 14A) for delivering a compressed implant device 3500 (e.g., a compressed heart valve) to a desired anatomical location in a patient and in an expanded state (FIG. 14B) for implantation and sealing of the implant device 3500 at the desired anatomical location. The embodiment of the delivery device 4000 depicted in FIGS. 14A-14B is similar in certain respects with the delivery device 3000 depicted in FIGS. 12A-12B, but differ in certain other respects.

As with the delivery device 3000 in FIGS. 12A-12B, the delivery device 4000 in FIGS. 14A-14B generally comprises a handle 3100, an outer sheath 3200, a delivery catheter 3300, an expandable implant device 3500 (e.g., heart valve) coupled to the delivery catheter 3200, and an inflatable balloon 3400 disposed at a distal end of the delivery catheter 3300. The delivery device 4000 differs from the delivery device 3000 in that the outer sheath 3200 is provided movably over the delivery catheter 3300 and a second balloon 3395 is provided between the expandable implant device 3500 (e.g., expandable heart valve) and the delivery catheter 3300. In the retracted state depicted in FIG. 14B, the second balloon 3395 is uninflated and the expandable implant device 3500 is compressed or crimped around the second balloon 3395 in a radially compressed configuration to fit within the outer sheath 3200.

FIG. 14A depicts the delivery device 4000 in a retracted position ready for delivering the compressed implant device 3500 (e.g., heart valve) close to or at a desired anatomical location for implantation. The outer sheath 3200 houses the delivery catheter 3300, the implant device 3500, the inflatable balloon 3400 and the second balloon 3395. A guide wire 3370 is provided with a nose cone 3375 at its distal tip to provide atraumatic guidance of the delivery catheter 3300 through the patient's vasculature or directly through the heart. Once the delivery device 4000 is appropriately positioned at or near the desired anatomical location for implantation, the outer sheath 3200 is retracted proximally to reveal the inflatable balloon 3400 and the expandable implant device 3500 compressed around the second balloon 3395. Inflation of the balloon 3400 and the second balloon 3395 can occur sequentially, with one of the inflatable balloon 3400 or the second balloon 3395 being inflated first and the other one of the inflatable balloon 3400 or the second balloon 3395 being inflated second. Optionally, the inflation of the balloon 3400 and the second balloon 3395 can occur simultaneously or about the same time.

The handle 3100 can comprise a single inlet port 3120 as depicted in FIGS. 12A-12B or it can comprise a plurality of inlet ports 3125, 3325 and 3375 through which the delivery catheter 3300, guide wire and the inflating fluid can be provided. In one embodiment, the delivery catheter 3300 can be advanced through the inlet port 3120, the guide wire 3370 can be advanced through the guide wire port 3375 and the inflating fluid used to inflate one or both of the inflatable balloon 3400 and the second balloon 3395 can be provide through the flush port 3325.

FIG. 14B depicts the delivery device 4000 in a fully deployed state for implanting the implant device 3500 at the desired anatomical location. As is shown, the outer sheath 3200 is retracted to expose the inflatable balloon 3400, the implant device 3500 and the second balloon 3395.

An energy source, such as a fiber optic 3310, can be movably provided within a lumen of the delivery catheter 3300 and can be advanced distally and into the balloon 3400 to emit a curing energy, such as UV light, by a sliding actuator 3110 on the handle 3100. The UV light can be used to cure the curable composition after the implant device 3500 has been implanted at the desired anatomical location and the curable composition has been provided between the implant device 3500 and the anatomical location.

Similarly with the delivery device 3000 in FIG. 12B, the UV light is emitted from the fiber optic 3310 at an angle θ relative to a central axis and the inflatable balloon 3400 can be provided to direct the emitted UV light to a desired location. The inflatable balloon 3400 can be configured to have a particular geometric configuration in which portions of the inflatable balloon 3400 are selected to reflect the emitted UV light and portions of the inflatable balloon 3400 are selected to transmit the emitted UV light.

Figure 15B:
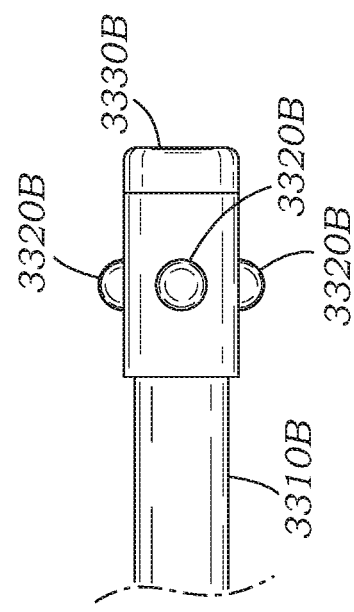
FIGS. 15A-15B depict optional embodiments of the tip of the energy source that is used to deliver the curing energy.
Figure 15A:
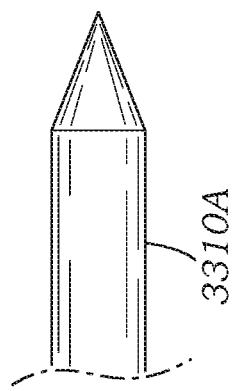

Optionally, the delivery device described above, the inflatable balloon 3400 can be made of an elastomeric material such as latex, polyurethane or polyisoprene. The reflective surface of the inflatable balloon 3400 can be provided by a reflective metallic coating on one or both of the external surface and the internal surface of the inflatable balloon 3400. The metallic coating can be made of a suitable material such as aluminum. In order to disperse the reflected light emitted from the fiber optic 3310, the tip of the fiber optic 3310 can be shaped. In one embodiment, the tip 3310A of the fiber optic 3310 can be provided in a conical shape, as shown in FIG. 15A to enable spreading of UV light. In another embodiment, the tip 3310B can be provided with a plurality of LED lights 3320B, as shown in FIG. 15B.

FIGS. 16A through 16D show an exemplary method of using the delivery device to apply a curing UV light using the balloon 3400 to cure a curable composition 5000 provided between an expandable implant device 3500 (e.g., heart valve) and the mitral valve annulus. Methods can use some or all of these steps as well as additional and/or modified steps. In the method depicted in FIGS. 16A through 16D, the delivery device accesses the mitral valve region from the left ventricle via the heart apex. Once the expandable implant device 3500 (e.g., heart valve) is implanted at the mitral valve annulus and the adhesive 5000 is provided between the mitral valve annulus and the expandable implant device 3500, the inflatable balloon 3400 is inflated with a fluid delivered through the flush port or lumen, depending on the configuration. In a preferred embodiment, the fluid is a liquid and more preferably a saline solution.

Figure 16A:
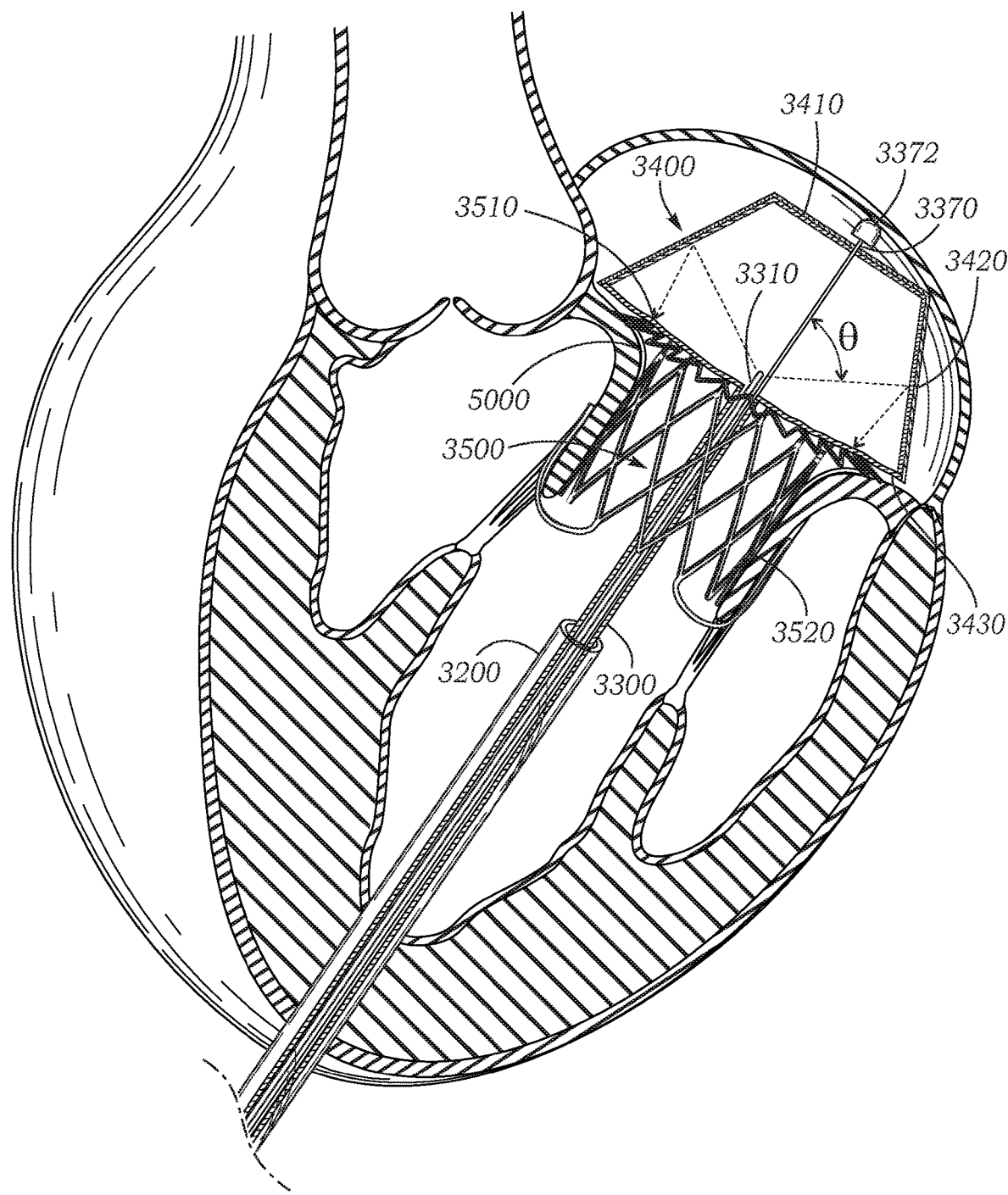
FIGS. 16A-16D depict exemplary steps of delivery curing energy to an implanted heart valve along the top sealing surface (FIG. 16A) and along the length of the stent body (FIGS. 16B-16D).

Once the inflatable balloon 3400 is fully inflated, the wide proximal end 3430 of the balloon is seated on top of the outer rim 3510 of the expandable implant device 3500, as shown in FIG. 16A. The fiber optic 3310 can then be advanced through the delivery catheter 3300 and into the inflatable balloon 3400 and can emit a curing UV light at an angle θ of about 22° to about 45° relative to a central axis. The UV light reflects off of the reflective surface 3420 of the inflatable balloon 3400, downward through the transmissive surface of the wide proximal end 3430 and onto the outer rim 3510 of the expandable implant device 3500. The UV light incident on the outer rim 3510 is effective to cure the curable composition 500 provided between the outer rim 3510 and the mitral valve annulus.

Figure 16B:
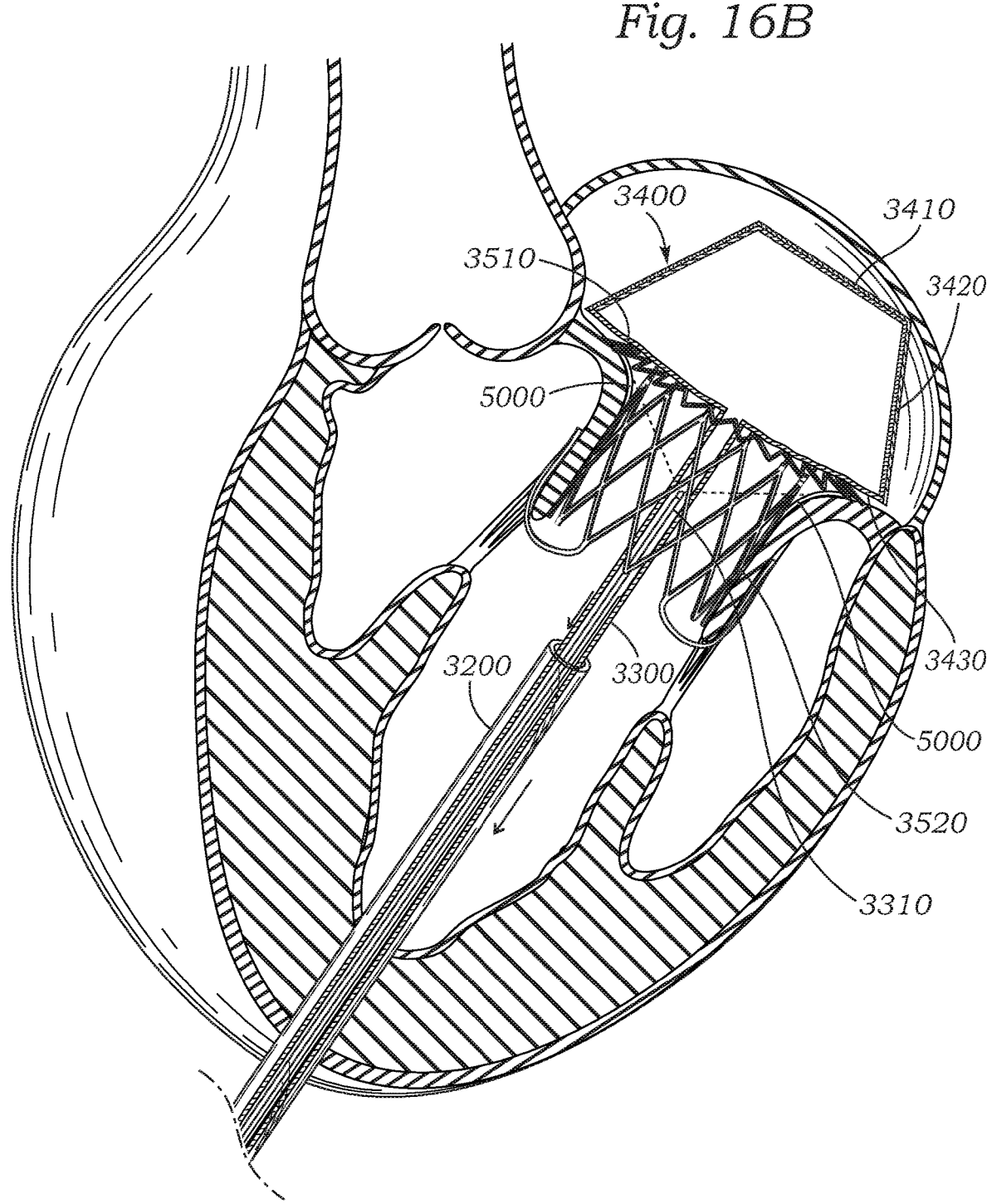
Figure 16C:
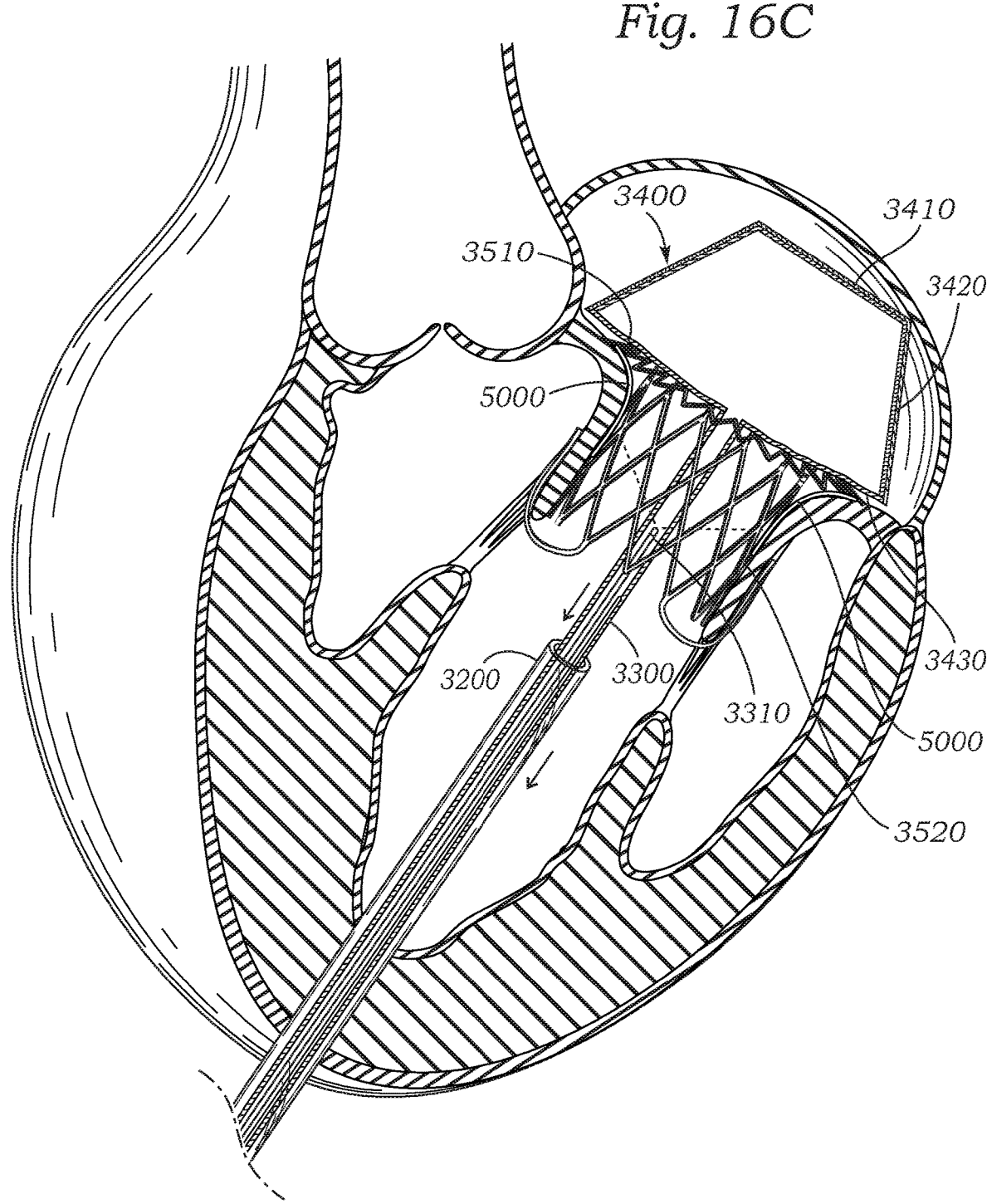
Figure 16D:
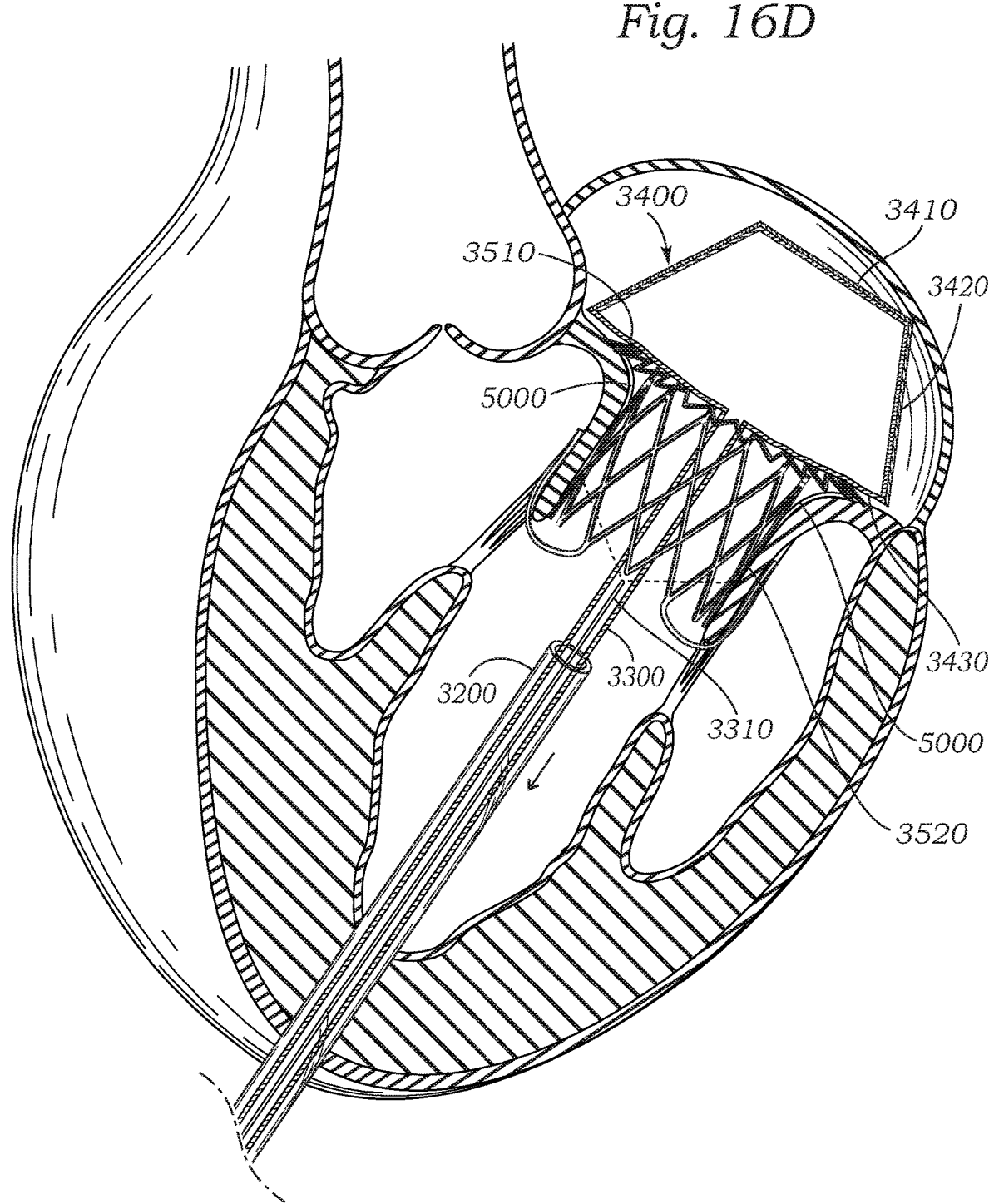

FIGS. 16B-16D depict the progressive retraction of the fiber optic 3310 proximally through the delivery catheter 3200 as the UV light is being emitted from the fiber optic 3310. In the embodiments depicted in FIGS. 16B-16D, at least a distal region of the delivery catheter 3200 is constructed of a light transmissive material such that it allows the UV light emitted from the fiber optic 3310 to be incident on the curable composition 5000 that is provided between the cylindrical stent body 3520 and the mitral valve annulus. Thus, as the fiber optic 3310 and the emitted UV light is moved proximally through the delivery catheter 3200, it cures the curable composition that is provided between the cylindrical stent body 3520 and the mitral valve annulus.

It is to be understood that the detailed description and specific examples, while indicating exemplary embodiments of the present disclosure, are given by way of illustration and not limitation. Many changes and modifications within the scope of the present disclosure can be made without departing from the spirit thereof, and the disclosure includes all such modifications. The principles described herein can be applied to other types of systems, implants, devices, features, aspects, methods, etc. While much of the discussion herein focuses on prosthetic heart valves and surgical methods, the invention is not so limited and principles, features, and steps described can be applied in other contexts. For example, another type of implant (e.g., a stent, graft, ring, etc.) can be used instead of a prosthetic heart valve and can optionally be implanted in other locations in the body or vasculature. Steps described with respect to methods involving surgical implantation of valves can be used in methods involving transcatheter or percutaneous implantation of valves and/or other implants.

The features and principles described with respect to one embodiment or variation herein can be used in other embodiments or variations. Methods or steps of methods described separately can be combined. In addition, where methods and steps described above indicate certain events occurring in certain order, the ordering of certain steps can be modified and that such modifications are in accordance with the variations of the invention. Additionally, certain of the steps can be performed concurrently in a parallel process when possible, as well as performed sequentially. Therefore, to the extent there are variations of the invention, which are within the spirit of the disclosure or equivalent to the inventions found in the claims, it is the intent that this patent will cover those variations as well.

The invention claimed is:

1. A method for implanting a bioprosthetic heart valve within a patient, the method comprising:
    positioning the bioprosthetic heart valve at an implant location inside the patient's body, wherein the bioprosthetic heart valve comprises a sewing ring and an anchoring skirt;
    applying a curable composition to one or more of the sewing ring, the anchoring skirt, and an anatomical feature of the implant location, the curable composition comprising a pre-polymer composition and a photoinitiator, wherein the pre-polymer composition is formed by a reaction of a polyol and a polyacid; and
    curing the curable composition for a cure time after the applying step;
    wherein the applying step is performed either before or after the positioning step;
    wherein one or both of the sewing ring and the anchoring skirt has a light transmittance of at least 5% therethrough; and
    wherein the curable composition fills a volume of space between the bioprosthetic heart valve and the anatomical feature to mitigate the occurrence of perivalvular leakage (PVL).

2. The method of claim 1, wherein:
    the bioprosthetic heart valve further comprises a support structure and one or more valve leaflets coupled to the support structure; and
    the support structure defines a central flow orifice.

3. The method of claim 2, wherein the bioprosthetic heart valve further comprises a stent frame having a first end coupled to the support structure and a second end extending away from the support structure, at least a portion of the stent frame being covered by a stent frame fabric.

4. The method of claim 3, wherein the applying is performed before the positioning.

5. The method of claim 4, wherein the applying is performed by one or a combination of:
    (1) dipping one or more of the support structure, a sewing portion, the stent frame, and the stent frame fabric into the curable composition;
    (2) applying the curable composition via an injector onto one or more of the support structure, the sewing portion, the stent frame, and the stent frame fabric;
    (3) applying a layer of the curable composition around one or more of the support structure, the sewing portion, the stent frame, and the stent frame fabric; and
    (4) applying a layer of the curable composition directly onto the anatomical feature.

6. The method of claim 1, wherein the applying is performed after the positioning.

7. The method of claim 6, wherein the applying is performed by one or a combination of:
    (1) applying the curable composition to an interface between the bioprosthetic heart valve and the anatomical feature; and
    (2) injecting the curable composition into an implant area between the bioprosthetic heart valve and the anatomical feature.

8. The method of claim 7, further comprising delivering an injector into the implant area between the bioprosthetic heart valve and the anatomical feature after the positioning and before the applying;
    wherein the applying comprises extruding the curable composition through the injector and into the implant area.

9. The method of claim 8, wherein an extruding tip portion of the injector is angled or hooked.

10. The method of claim 9, wherein:
    the bioprosthetic heart valve comprises a central flow orifice;
    the extruding tip portion is hooked; and
    the extruding tip portion is passed through the central flow orifice of the bioprosthetic heart valve and is positioned either at the interface between the bioprosthetic heart valve and the anatomical feature or between the bioprosthetic heart valve and the anatomical feature.

11. The method of claim 1, wherein the curing is performed in the presence of one of an electromagnetic energy and thermal energy.

12. The method of claim 11, wherein the electromagnetic energy is UV light.

13. The method of claim 1, wherein the cure time is selected from the group consisting of: less than 30 seconds, less than 20 seconds, less than 10 seconds, less than 5 seconds and less than 2 seconds.

14. The method of claim 1, wherein:
one or both of the sewing ring and the anchoring skirt is made of a porous material or an open-weave material that permits a transmittance of electromagnetic energy therethrough.

15. The method of claim 14, wherein:
one or both of the sewing ring and the anchoring skirt is made of an open-weave fabric; and
the transmittance is selected from the group consisting of: at least 10%, at least 20%, at least 30%, at least 40%, at least 50%, at least 60%, at least 70%, at least 80%, at least 90%, and 100%.

16. The method of claim 1, wherein:
the curable composition is a sealant; and
a seal is formed between the bioprosthetic heart valve and the anatomical feature following curing.

17. The method of claim 1, wherein:
the curable composition is an adhesive; and
the bioprosthetic heart valve is secured to the anatomical feature without sutures after the curing.

18. The method of claim 1, wherein the bioprosthetic heart valve further comprises a peripheral sewing portion.

19. The method of claim 1, wherein, in the applying step, the curable composition is applied to the anatomical feature.

20. The method of claim 19, wherein the applying is performed before the positioning.

21. The method of claim 19, wherein the applying is performed after the positioning.

22. The method of claim 1, wherein one or both of the sewing ring and the anchoring skirt comprises a material selected from the group consisting of: a transparent fabric, a porous fabric, a woven fabric, and an open-weave fabric.

23. The method of claim 1, wherein the polyol is one or more selected from the group consisting of: a diol, an alkane diol, a triol, a glycerol, a trimethylolpropane, a triethanolamine, a tetraol, an erythritol, a pentaerythritol, a sorbitol, an unsaturated diol, a tetradeca-2,12-diene-1,1,14-diol, a macromonomer diol, a polyethylene oxide, and a N-methyldiethanolamine.

24. The method of claim 1, wherein the polyacid is selected from the group consisting of: glutaric acid, adipic acid, pimelic acid, suberic acid, sebacic acid, and azelaic acid.

25. The method of claim 1, wherein:
the polyol is a glycerol; and
the polyacid is a sebacic acid.

26. The method of claim 25, wherein the pre-polymer composition is prepared through the polycondensation of equimolar amounts of the glycerol and the sebacic acid.

27. The method of claim 1, wherein the photoinitiator is selected from the group consisting of: 2-dimethoxy-2-phenyl-acetophenone, 2-hydroxy-1-[4-(hydroxyethoxy)phenyl]-2-methyl-1-propanone, 1-hydroxycyclohexyl-1-phenyl ketone, 2-hydroxy-2-methyl-1-phenyl-1-propanone, 2-benzyl-2-(dimethylamino)-1-[4-morpholinyl)phenyl]-1-butanone, methylbenzoylformate, oxy-phenyl-acetic acid-2-[2-oxo-2-phenyl-acetoxy-ethoxy]-ethyl ester, 2-methyl-1-[4-(methylthio)phenyl]-2-(4-morpholinyl)-1-propanone, diphenyl(2,4,6-trimethylbenzoyl)-phosphine oxide, phosphine oxide, and phenyl bis(2,4,6-trimethyl benzoyl).

28. The method of claim 16, wherein the bioprosthetic heart valve is secured to the implant location using sutures or staples.

29. The method of claim 16, wherein the sealant has an adhesive strength of less than about 0.5 N/cm$^2$.

30. The method of claim 16, wherein the pre-polymer composition has a degree of activation that is 0.5 or less.

31. The method of claim 16, wherein the sealant has a crosslinking density of about 10% or less.

32. The method of claim 17, wherein the adhesive has a crosslinking density of about 15% or more.

33. The method of claim 17, wherein the pre-polymer composition has a degree of activation of 0.6 or greater.

* * * * *